US012575973B1

(12) United States Patent
El Sherif et al.

(10) Patent No.: US 12,575,973 B1
(45) Date of Patent: Mar. 17, 2026

(54) FACIAL SHIELD WITH ADJUSTABLE LAMP AND GLARE SHIELD

(71) Applicant: Pabban Development, Inc., Irvine, CA (US)

(72) Inventors: Dina El Sherif, Irvine, CA (US); Jacob Herbert, Irvine, CA (US)

(73) Assignee: Pabban Development, Inc., Irvine, CA (US)

( * ) Notice: Subject to any disclaimer, the term of this patent is extended or adjusted under 35 U.S.C. 154(b) by 0 days.

(21) Appl. No.: 19/292,211

(22) Filed: Aug. 6, 2025

Related U.S. Application Data

(60) Provisional application No. 63/748,023, filed on Jan. 22, 2025.

(51) Int. Cl.
| | |
|---|---|
| *A61F 9/02* | (2006.01) |
| *A62B 7/10* | (2006.01) |
| *F21L 4/00* | (2006.01) |

(52) U.S. Cl.
CPC ................ *A61F 9/025* (2013.01); *A62B 7/10* (2013.01); *F21L 4/00* (2013.01)

(58) Field of Classification Search
CPC ....... F41H 5/06; A41D 13/1184; A41D 13/11; F21V 33/008; F21V 33/0068
See application file for complete search history.

(56) References Cited

U.S. PATENT DOCUMENTS

| | | | |
|---|---|---|---|
| 2,638,593 A | 5/1953 | Eloranta | |
| 2,881,443 A | 4/1959 | Barker | |
| 3,214,767 A | 11/1965 | Weber | |
| 3,295,143 A | 1/1967 | Hoffman | |
| 4,530,112 A | * 7/1985 | Cecala | A42B 3/225 |
| | | | 362/105 |
| 4,856,109 A | 8/1989 | Desy et al. | |
| 5,206,956 A | 5/1993 | Olson | |
| 5,247,706 A | 9/1993 | Mark | |
| 5,694,925 A | 12/1997 | Reese et al. | |

(Continued)

FOREIGN PATENT DOCUMENTS

| | | | | |
|---|---|---|---|---|
| DE | 102020112736 A1 | * 11/2021 | ......... | A41D 13/1184 |
| GB | 2591870 A | 8/2021 | | |

(Continued)

OTHER PUBLICATIONS

Innovation Q+ NPL Search (Year: 2025).*

*Primary Examiner* — Anabel Ton
(74) *Attorney, Agent, or Firm* — BLAIR WALKER IP SERVICES, LLC

(57) ABSTRACT

A system includes a support configured to be carried by the head of a user, a facial shield configured to be coupled to the support such that the facial shield is maintained anterior to the face of the user, the facial shield having substantial clarity for viewing therethrough, the facial shield further including an outer surface and an inner surface, an emitted-light source configured to be carried between the facial shield and the user and configured to provide a light beam that is able to at least partially radiate through the facial shield, and a flexible elongate opaque sheet having a first end coupled to the emitted-light source and a free second end configured to maintain contact with the inner surface of the facial shield as the light beam is angularly adjusted over a working adjustment angle range.

30 Claims, 25 Drawing Sheets

(56)        References Cited

U.S. PATENT DOCUMENTS

| | | | |
|---|---|---|---|
| 5,704,349 | A | 1/1998 | Hubbard et al. |
| 7,093,302 | B1 * | 8/2006 | Burns ........................ A61F 9/06 |
| | | | 2/9 |
| 7,192,151 | B2 * | 3/2007 | Clupper .................. F21L 14/00 |
| | | | 362/105 |
| 7,431,453 | B2 * | 10/2008 | Hogan ................... G02C 7/088 |
| | | | 351/158 |
| D589,545 | S | 3/2009 | Murphy et al. |
| D600,728 | S | 9/2009 | Braganca et al. |
| 7,725,949 | B2 | 6/2010 | Landis |
| 8,215,791 | B2 | 7/2012 | Feinbloom et al. |
| 8,851,709 | B2 | 10/2014 | Feinbloom et al. |
| 9,945,538 | B2 | 4/2018 | Beausoleil |
| 9,949,517 | B2 | 4/2018 | Howard |
| 10,052,233 | B2 | 8/2018 | Yang et al. |
| 10,401,620 | B1 | 9/2019 | Stratton et al. |
| 10,687,568 | B2 * | 6/2020 | Pavalarajan ........ H04L 25/4908 |
| 11,412,792 | B2 * | 8/2022 | Keene ........................ A61L 9/20 |
| 2005/0047117 | A1 * | 3/2005 | Scholl ........................ A61F 9/06 |
| | | | 362/106 |
| 2005/0190549 | A1 * | 9/2005 | Donaldson ............. A42B 3/225 |
| | | | 362/105 |
| 2014/0362561 | A1 * | 12/2014 | Faircloth ................ G02C 11/04 |
| | | | 362/103 |
| 2021/0298391 | A1 * | 9/2021 | Keene ................ A41D 13/1107 |
| 2021/0368887 | A1 * | 12/2021 | Nguyen ................. A41D 1/002 |

FOREIGN PATENT DOCUMENTS

| | | | | |
|---|---|---|---|---|
| WO | WO-2014160149 | A2 * | 10/2014 | ........... A62B 18/045 |
| WO | WO 2022/087247 | A1 | 4/2022 | |

* cited by examiner

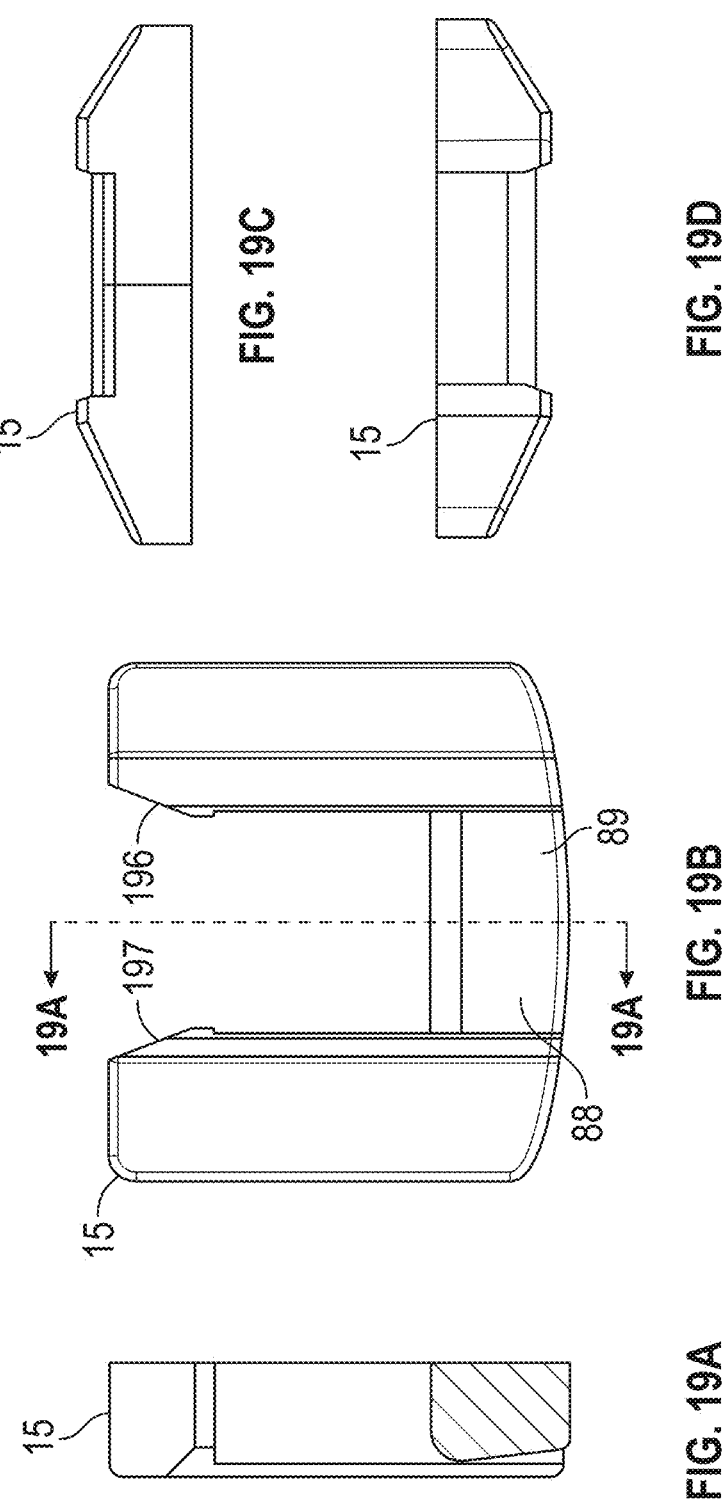

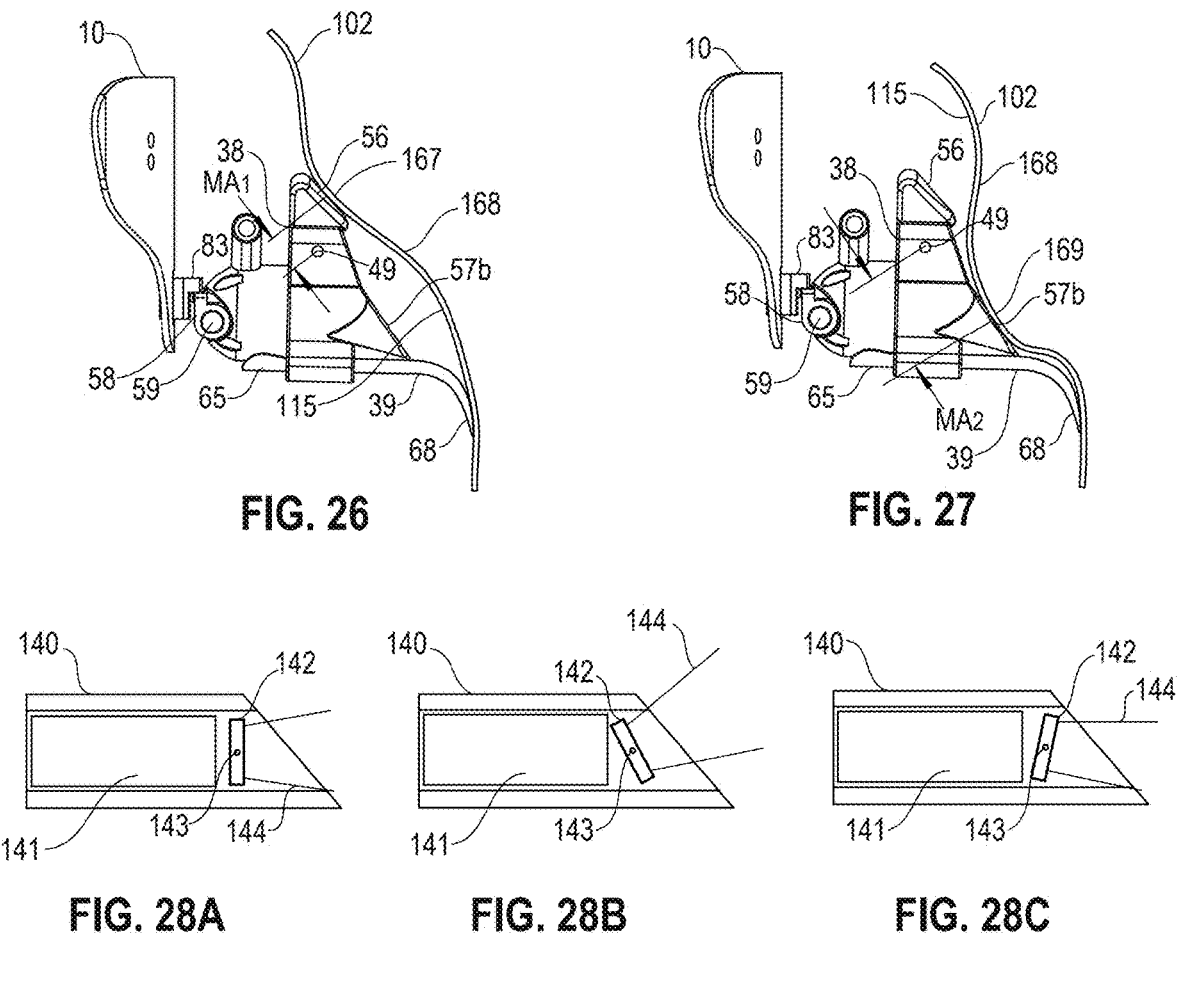
FIG. 26
FIG. 27
FIG. 28A
FIG. 28B
FIG. 28C
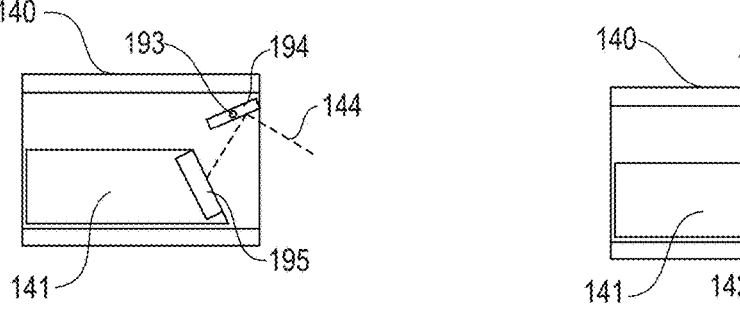
FIG. 28D
FIG. 28E

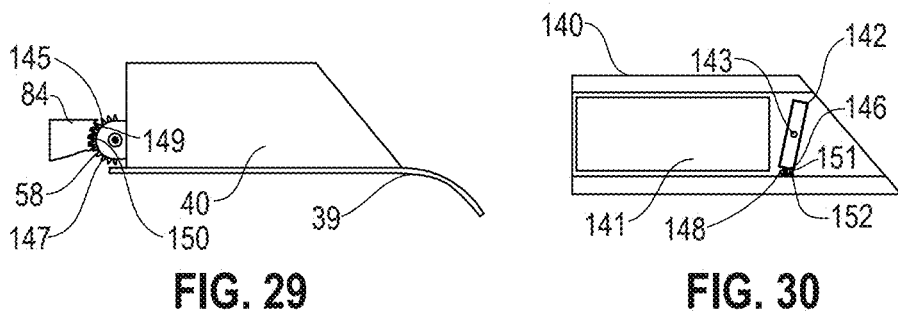
FIG. 29            FIG. 30
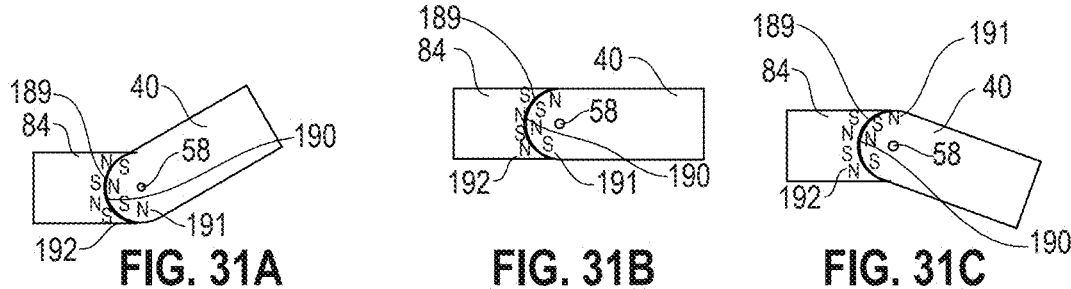
FIG. 31A        FIG. 31B        FIG. 31C
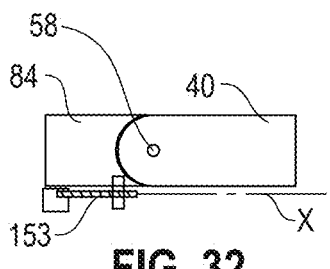
FIG. 32

FACIAL SHIELD WITH ADJUSTABLE LAMP AND GLARE SHIELD

INCORPORATION BY REFERENCE TO ANY PRIORITY APPLICATIONS

This application claims the benefit of priority to U.S. Provisional Patent Application No. 63/748,023, filed on Jan. 22, 2025, which is incorporated by reference herein in its entirety for all purposes. Priority is claimed pursuant to 35 U.S.C. § 119.

BACKGROUND OF THE INVENTION

Field of the Invention

The field of the invention generally relates to personal protection systems, including, but not limited to personal environmental protections systems. The personal protections systems often include a headgear structure which is worn by an individual to protect from particulate material. The personal protection systems may provide filtered air to the user. The personal protection system comprises an adjustable lamp. The personal protection system comprises a glare shield configured to cooperate with the adjustable lamp.

SUMMARY OF THE INVENTION

In one embodiment of the present disclosure, a system includes a support configured to be carried by the head of a user, a facial shield configured to be coupled to the support such that the facial shield is maintained anterior to the face of the user, the facial shield having substantial clarity for viewing therethrough, the facial shield further including an outer surface and an inner surface, an emitted-light source configured to be carried between the facial shield and the user and configured to provide a light beam that is able to at least partially radiate through the facial shield, a pivot coupled to the emitted-light source, the pivot configured to provide at least some rotation about a pivot axis having a substantially horizontal extension, to angulate the light beam superiorly or inferiorly, and a contact surface carried on the emitted-light source and capable of being contacted by the inner surface of the facial shield when the facial shield is coupled to the support and the support is carried by the head of the user, wherein when a first force placed on the outer surface of the facial shield at a first location in relation to the contact surface causes the emitted-light source to angulate the light beam superiorly, and wherein when a second force placed on the outer surface of the facial shield at a second location in relation to the contact surface causes the emitted-light source to angulate the light beam inferiorly.

In another embodiment of the present disclosure, a system includes a support configured to be carried by the head of a user, a facial shield configured to be coupled to the support such that the facial shield is maintained anterior to the face of the user, the facial shield having substantial clarity for viewing therethrough, the facial shield further including an outer surface and an inner surface, an emitted-light source configured to be carried between the facial shield and the user and configured to provide a light beam that is able to at least partially radiate through the facial shield, and a flexible elongate opaque sheet having a first end coupled to the emitted-light source and a free second end configured to maintain contact with the inner surface of the facial shield as the light beam is angularly adjusted over a working adjustment angle range.

BRIEF DESCRIPTION OF THE DRAWINGS

FIG. 19A is a cross-sectional view of a stop taken along line A-A of FIG. 19B, according to an embodiment of the present disclosure.

FIG. 19B is an elevation view of the stop, according to an embodiment of the present disclosure.

FIG. 19C is a first side view of the stop, according to an embodiment of the present disclosure.

FIG. 19D is a second side view of the stop, according to an embodiment of the present disclosure.

FIG. 26 is a side view of the adjustable lamp and glare shield assembly of FIG. 20 being adjusted upwardly.

FIG. 27 is a side view of the adjustable lamp and glare shield assembly of FIG. 20 being adjusted downwardly.

FIG. 28A is a sectional view of a lamp having a pivotable lens in a first position, according to an embodiment of the present disclosure.

FIG. 28B is a sectional view of a lamp having a pivotable lens in a second position, according to an embodiment of the present disclosure.

FIG. 28C is a sectional view of a lamp having a pivotable lens in a third position, according to an embodiment of the present disclosure.

FIG. 28D is a section view of a lamp having a pivotable mirror, according to an embodiment of the present disclosure.

FIG. 28E is a section view of a lamp having a pivotable lens and a pivotable mirror, according to an embodiment of the present disclosure.

FIG. 29 is a side view of an adjustable lamp and glare shield, according to an embodiment of the present disclosure.

FIG. 30 is a side view of an adjustable lamp and glare shield, according to an embodiment of the present disclosure.

FIGS. 31A-31C are side views of an adjustable lamp and glare shield, according to an embodiment of the present disclosure.

FIG. 32 is a side view of an adjustable lamp and glare shield, according to an embodiment of the present disclosure.

DETAILED DESCRIPTION OF THE ILLUSTRATED EMBODIMENTS

There are several types of air flow, filtration and protective systems which are known in the art. Several types of such systems are currently available on the market for use in surgical arenas, in "clean room" environments, or in hazardous/contaminated environments.

Some of the existing systems include hoods, gowns, filters, and the like. In some instances, the air filters are built into the helmet structure. Known units frequently include external sources of air such as gas cylinders, air lines or the like which are connected to the helmet structure by tubes, hoses or the like. Currently available lens/facial seal combinations, sometimes known as loose fitting hoods, are expensive to manufacture due to the geometries required for the facial seal to attach to the lens which is curved in a plane perpendicular to the seal to the face/head of the wearer. Improvements described herein related to the interface between facial shields and headgear (helmets, etc.) accommodate clean or sterile donning techniques, and improve the overall ease of donning the protective equipment and garments. In sterile procedures, any improvements that lower or minimize contact, or decomplicate the donning steps can significantly improve the likelihood of achievement and maintenance of sterility. These improvements can also minimize unnecessary contamination to other sites. The systems described herein can also be utilized for general healthcare use or general laboratory use, as well as in surgery, medical procedure, dental use, firefighting use, or industrial use, such as welding, mining, or other manufacturing. The systems can comprise PAPR (Powered Air Purifying Respirator) systems comprising a blower with a motor, but can also comprise non-powered systems, including physical or acoustic protection systems, such as those used in construction or airport or raceway communication and/or protection. The systems described herein can also be utilized in general PPE (personal protective equipment). The embodiments disclosed herein have application in any system that utilizes a facial shield through which the wearer can view the exterior. The facial shield can be for protection against any environmental or work-related danger or irritant, such as splashes, impact, or wind.

Some of the existing systems include hoods, gowns, filters, and the like. In some instances, the air filters are built into the helmet structure. Known units frequently include external sources of air such as gas cylinders, air lines or the like which are connected to the helmet structure by tubes, hoses or the like. Other systems do not have hoses, such as "no hose" respirators and "no hose" powered air purifying respirators.

Figure 1:
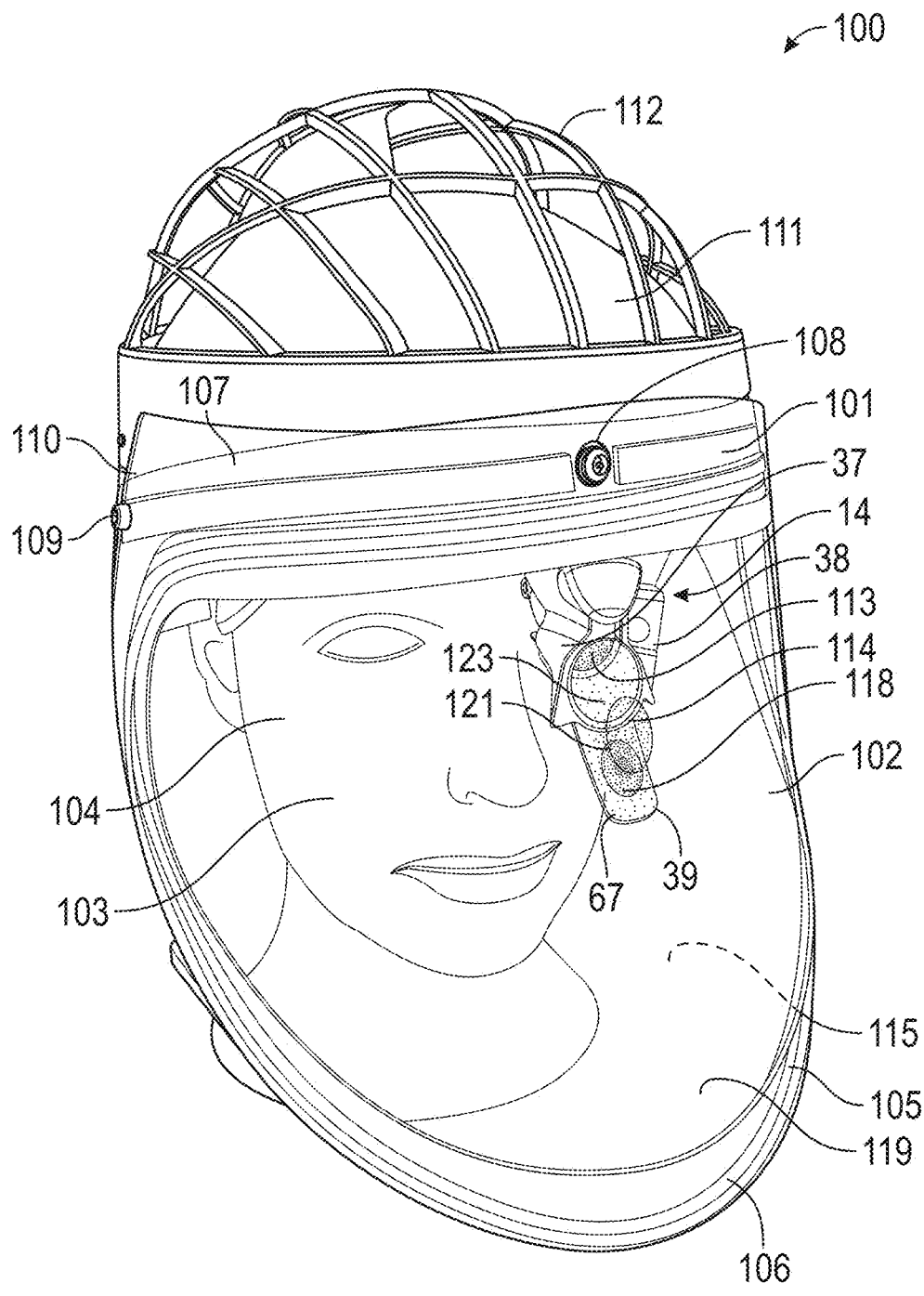
FIG. 1 is a first perspective view of a personal protection assembly on a user's head, according to an embodiment of the present disclosure.
Figure 2:
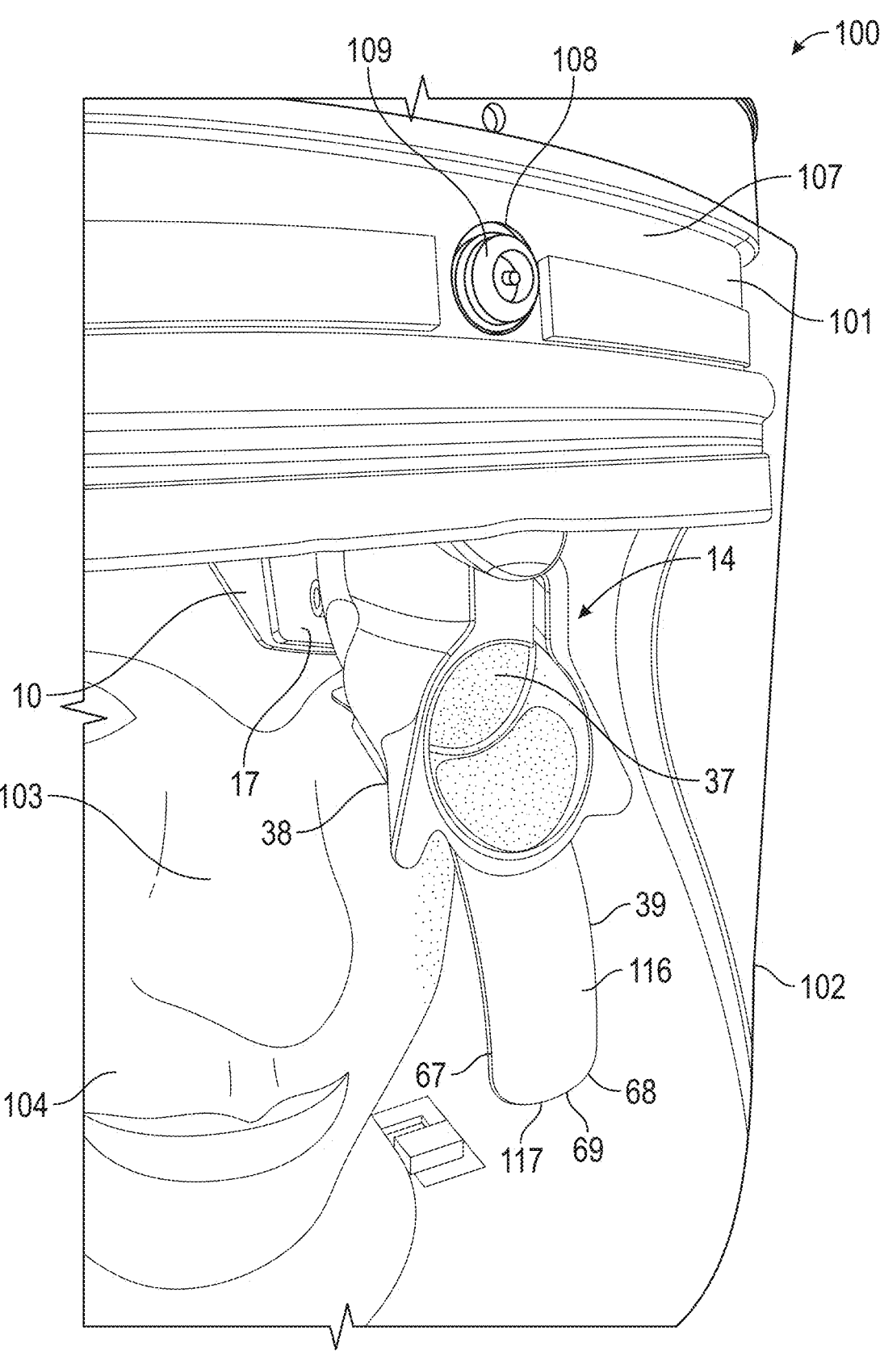
FIG. 2 is a detailed perspective view of the personal protection assembly of FIG. 1 on a user's head, according to an embodiment of the present disclosure.

FIGS. 1-2 illustrate a personal protection system 100 comprising a liner 101 and a clear, translucent facial shield 102 for the user 103 to see clearly through. The facial shield 102 is configured to completely protect an anterior portion of the head 104 of the user 103 from possible contamination as the user 103 performs a surgical or other medical procedure. In some embodiments, the personal protection system 100 is configured to be used by a user 103 that can comprise any type of medical personnel, or support personnel. The facial shield 102 includes a seam 105 having an outer perimeter 106. The facial shield 102 includes an upper portion 107 having a plurality of holes 108 that are configured to removably snap onto pins, buttons, or posts 109 that are attached around an outer perimeter 110 of the liner 101. The liner 101 includes open areas (not shown) through which air can enter. A hemispheric-shaped filter 111 is placed over the liner 101. Air is able to enter through the open areas and pass through the filter 111, for example when forced in via one or more fan. A filter holder 112 engages a top portion of the filter 111 to maintain it in place. A helmet (not shown) can be attached on top of the filter holder 112. The helmet can be configured to attach to the fan or other type of air mover. The facial shield 102 in some embodiments is surrounded by fabric or sheet material that can form a hood, gaiter, gown, toga, or shroud, to thus partially or fully isolate the air space around the user's head or head and body. Sheet material can be configured to be carried by the helmet.

Figure 3:
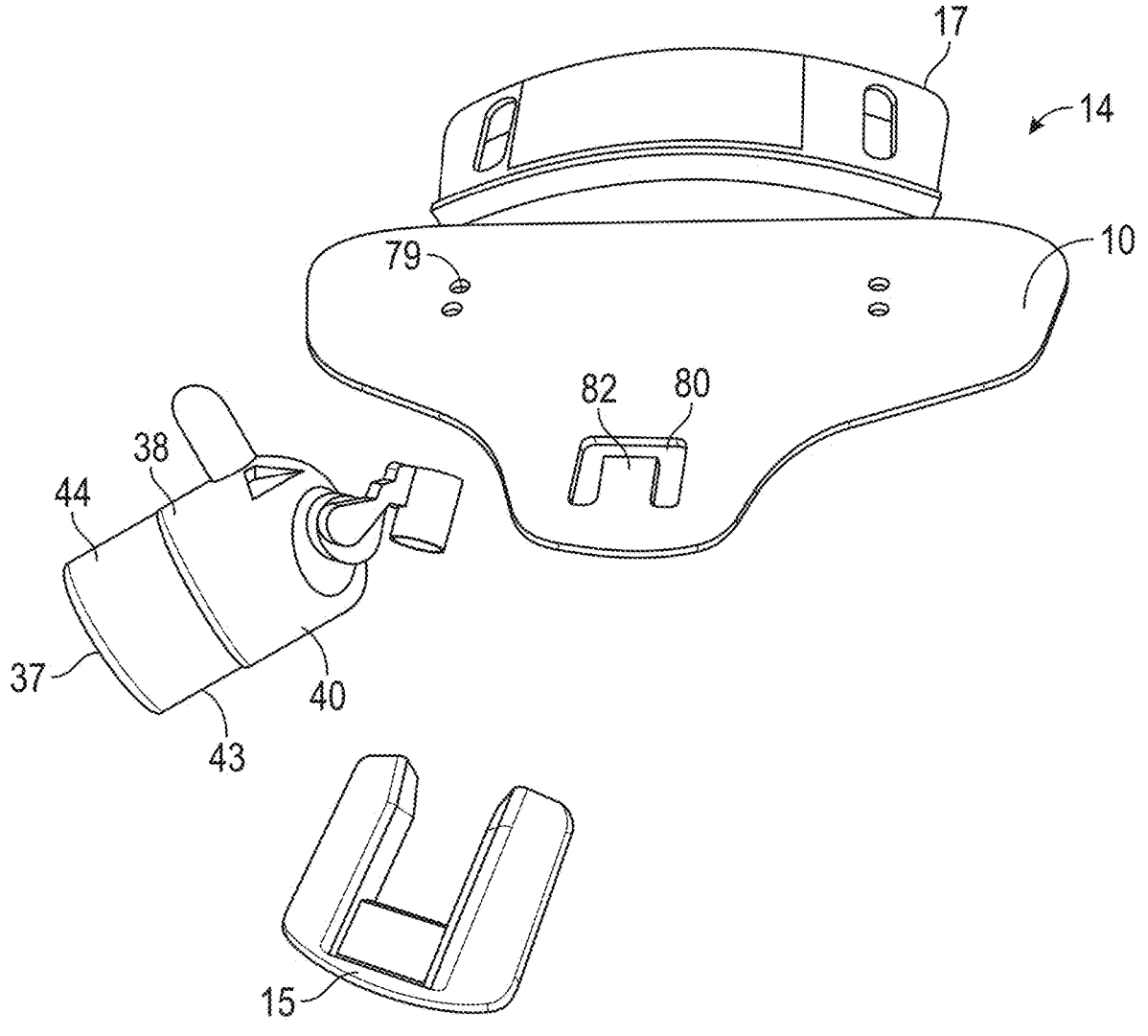
FIG. 3 is an exploded view of components of an adjustable lamp and glare shield assembly of the personal protection assembly of FIG. 1, according to an embodiment of the present disclosure.
Figure 4:
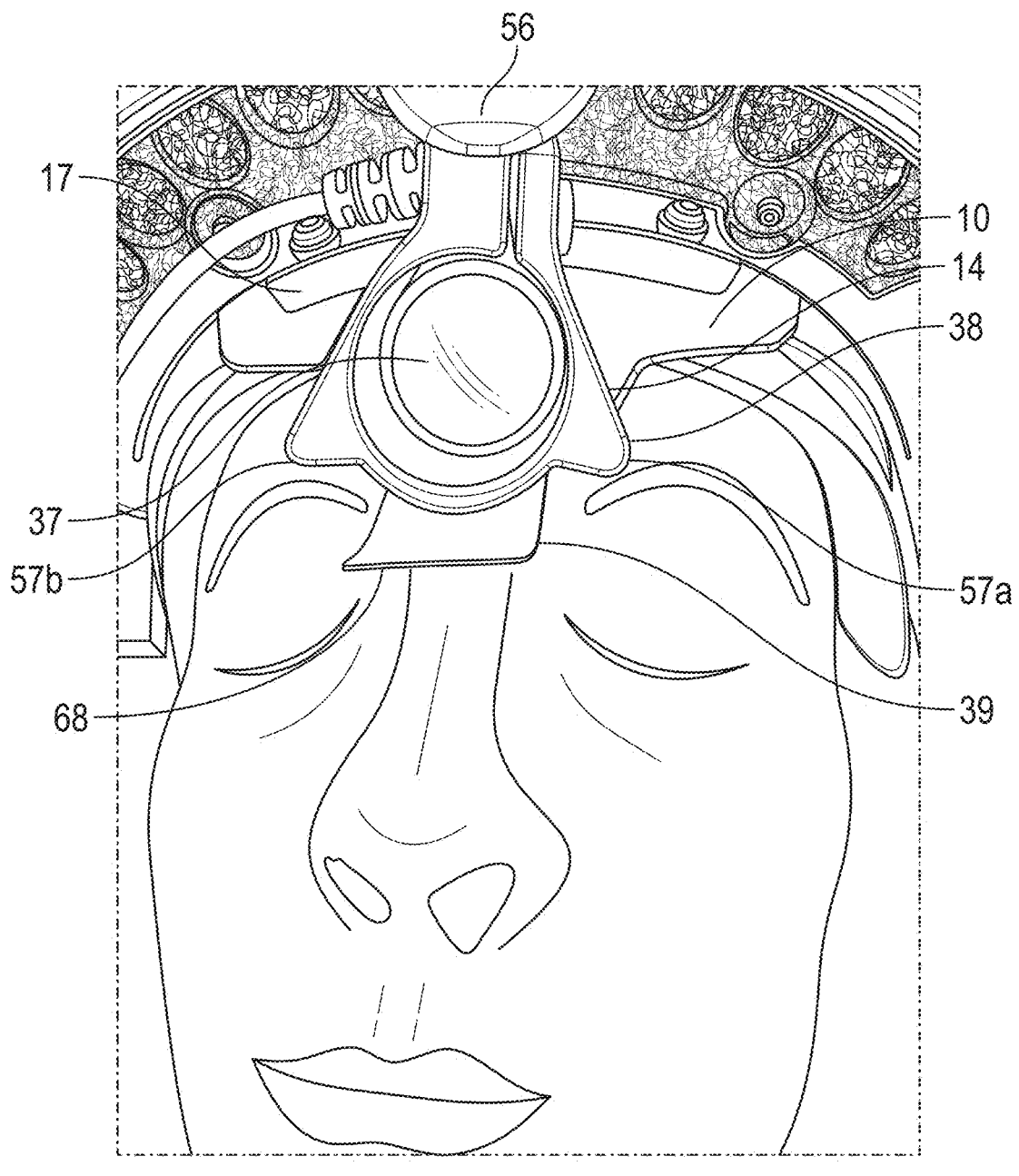
FIG. 4 is a front view of the personal protection assembly on a user's head, according to an embodiment of the present disclosure.
Figure 5:
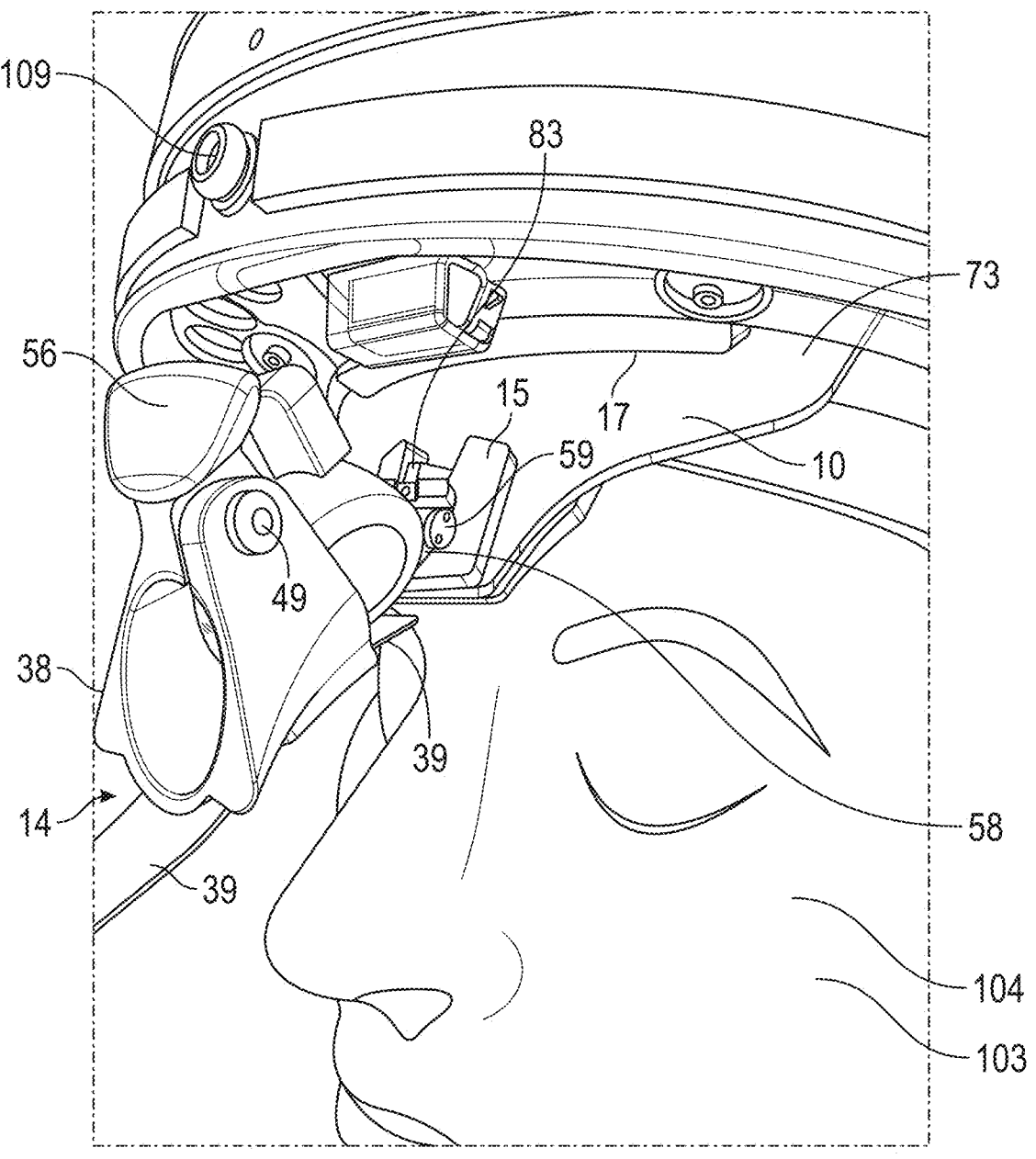
FIG. 5 is a front-to-side view of the personal protection assembly on a user's head, according to an embodiment of the present disclosure.
Figure 6:
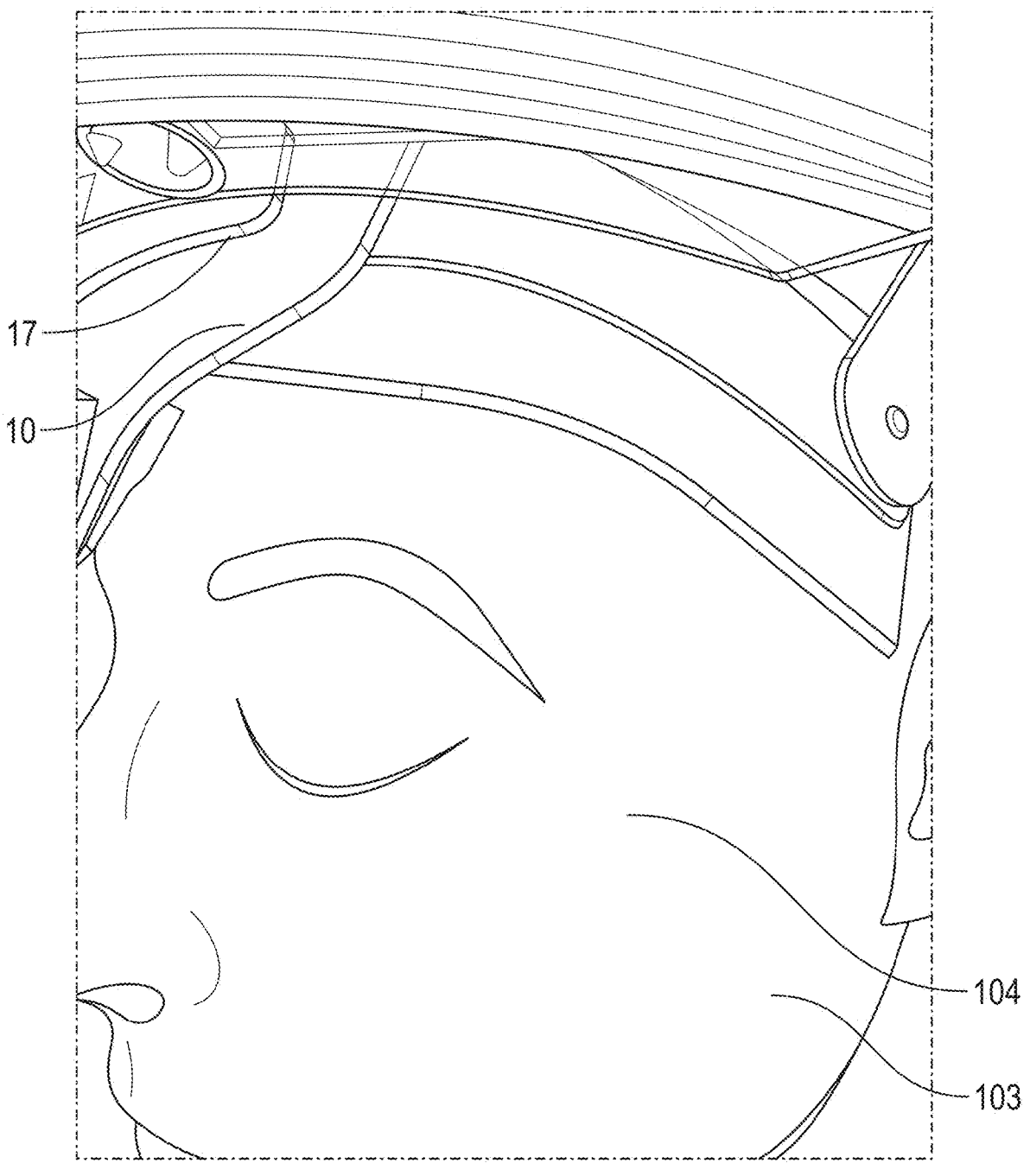
FIG. 6 is a side view of the personal protection assembly on a user's head, according to an embodiment of the present disclosure.
Figures 7, 8:
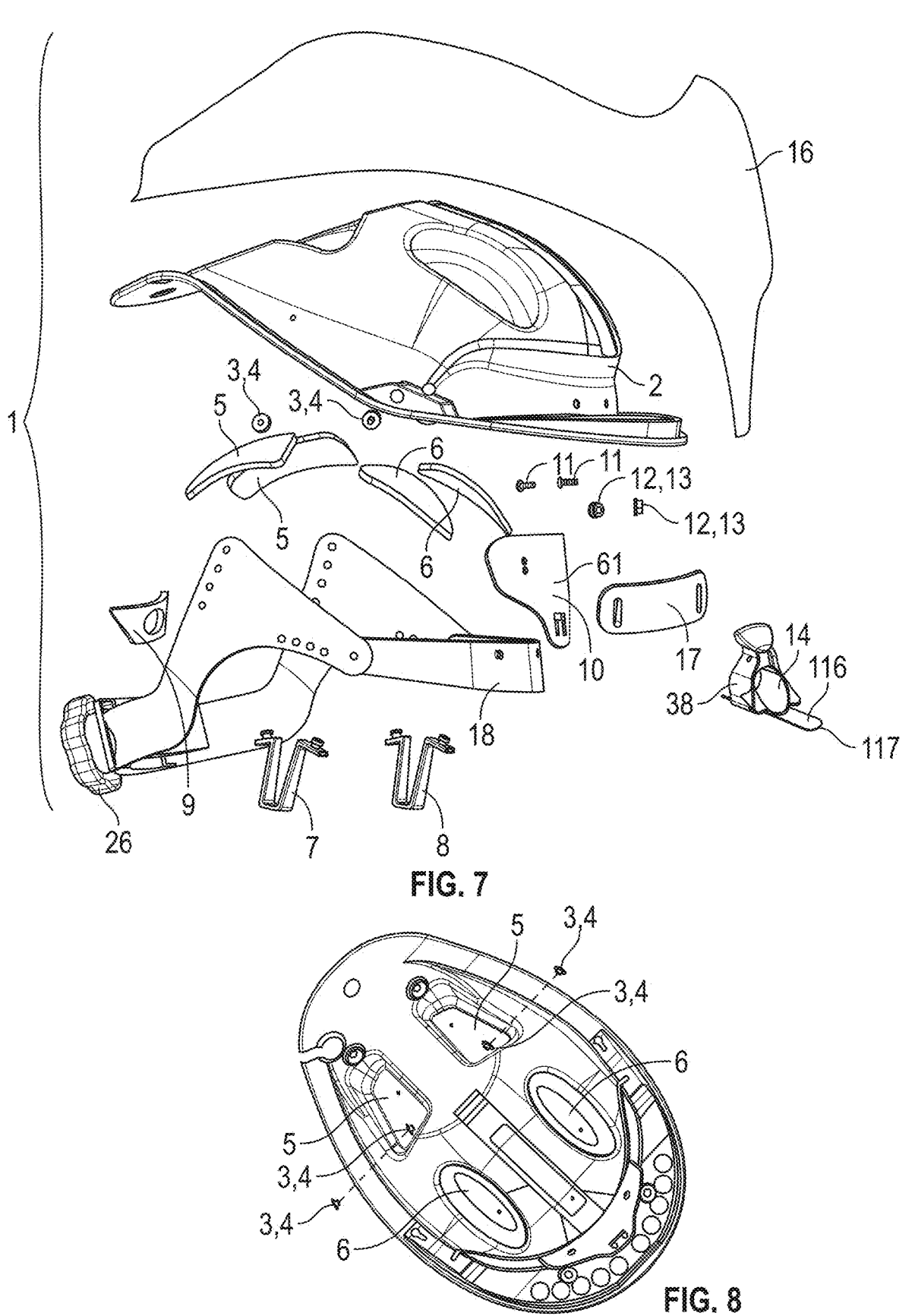
FIG. 7 is an exploded perspective view of another embodiment of a personal protection system, according to an embodiment of the present disclosure.
FIG. 8 is bottom view of a liner, bracket, and headband assembly of the personal protection system of FIG. 7, according to an embodiment of the present disclosure.
Figure 9:
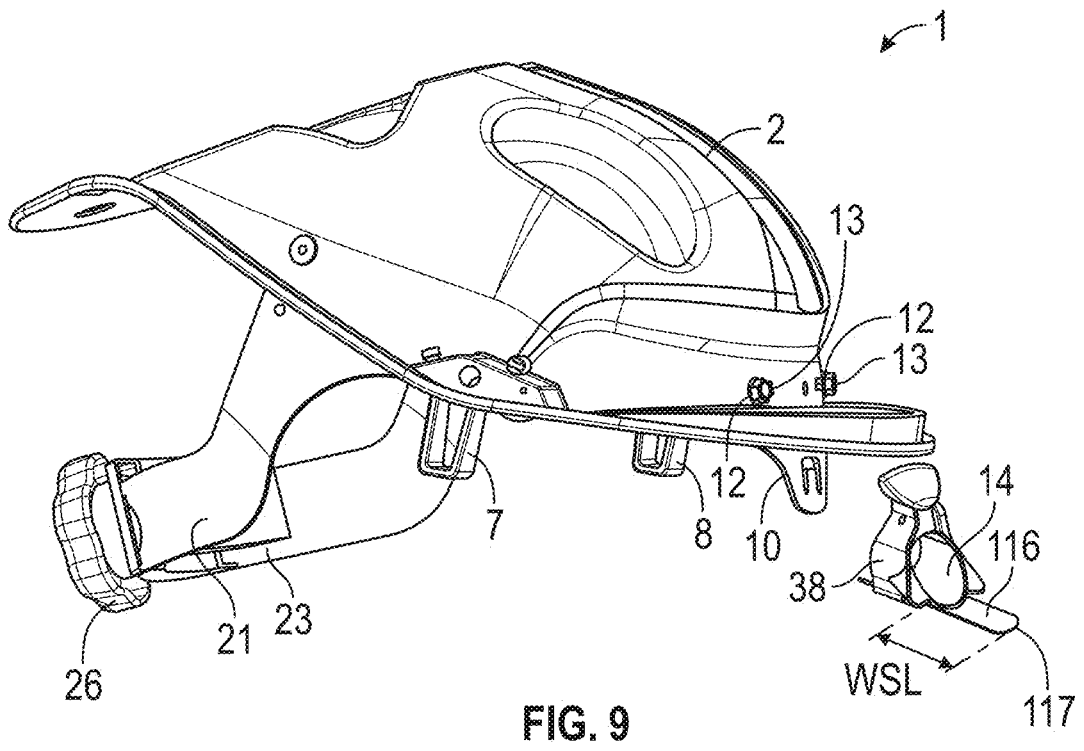
FIG. 9 is a perspective view of a portion of the personal protection system of FIG. 7, according to an embodiment of the present disclosure.
Figure 10:
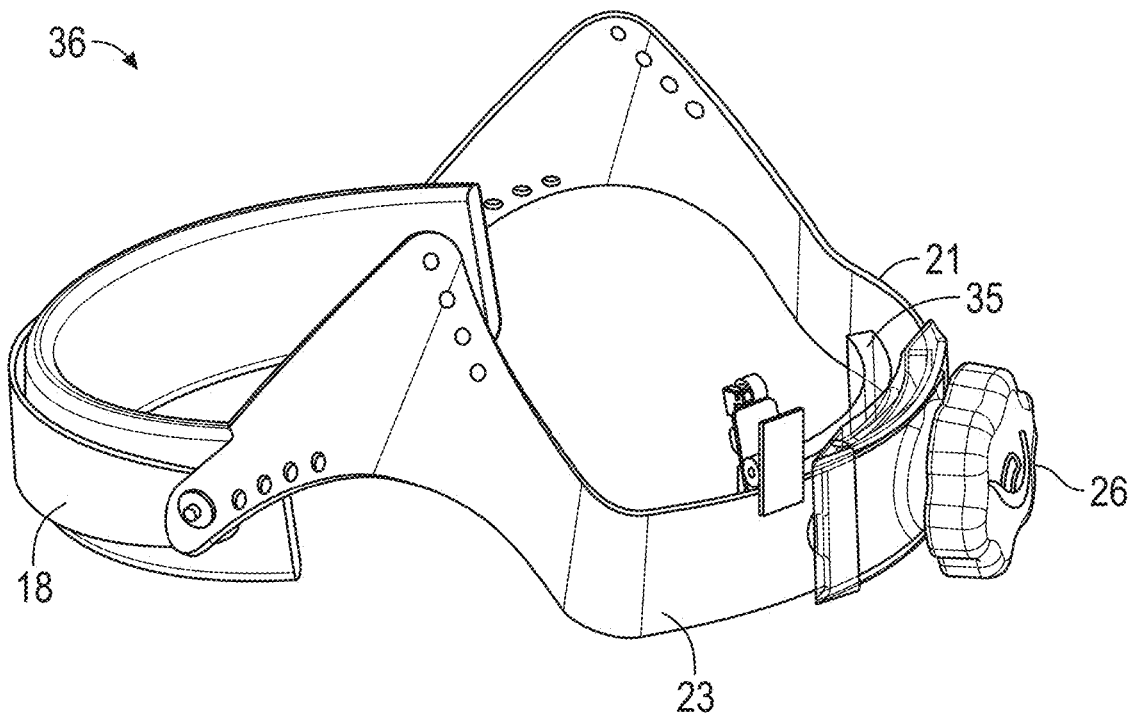
FIG. 10 is a perspective view of a headband assembly of the personal protection system of FIG. 7, according to an embodiment of the present disclosure.

FIG. 3 illustrates components of an adjustable lamp and glare shield assembly 14. The assembly 14 includes a bracket 10, a spacer 17, a stop 15, a lamp 37, and an adjustable lamp holder 38. The assembly 14 further includes a flexible tongue 39, as shown in FIG. 4. The flexible tongue 39 comprises a flexible sheet of opaque material. In some embodiments, the sheet of opaque material comprises a black polycarbonate having a thickness of about 0.002 inch to about 0.020 inch, or about 0.006 inch to about 0.015 inch, or about 0.002 inch to about 0.012 inch, or about 0.006 inch to about 0.008 inch. The flexible tongue 39 is an elongate sheet having an adjustable working section length WSL (FIG. 9). The working section length WSL comprises the portion that extends from the adjustable lamp holder 38, and is configured to be deflectable as a beam. Because of the combination of material flexibility and working section length WSL, the deflection can comprise an arced bending shape, as will be described in more detail. The adjustable working section length WSL can in some embodiments be adjusted between about 1.5 inches and about 2.5 inches, or between about 1.8 inches and about 2.2 inches. The width W of the flexible tongue 39 (FIG. 16C) along the working section length WSL is between about 0.5 inch and about 1.0 inch, and can be configured to have a maximum width of about 0.9 inches, or about 0.75 inches, or about 0.65 inches. The stiffness of the beam in deflection can also be controlled by providing some curvature of the flexible tongue 39 in relation to a longitudinal axis A, as will be described in more detail. The adjustable lamp holder 38 is configured to provide this curvature via a curved slit or slot (such as cavity 62 of FIGS. 15A and 15E) into which the flexible tongue 39 can slide longitudinally. In other embodiments, the flexible tongue 39 comprises another polymer, such as polyester, polyamide, polyether ether ketone (PEEK), or polyimide. In some alternative embodiments, the flexible tongue 39 comprises a substantially translucent material, such as a substantially translucent polymeric material, but is coated on one side/face or both sides/faces with an opaque coloring, such as an ink, or opaque tape.

In FIG. 1, the lamp 37 includes a lens 113 out of which a light beam 114 radiates. The lamp 37 is configured such that the light beam 114 illuminates a working area in front of the user that is in the user's visual field. For example, the working area can comprise a surgical working area on a patient's body that is in position on a surgical table. The surgical working area can be, for example, about 10 inches to about 24 inches from the eyes of the user, or about 12 inches to about 16 inches from the eyes of the user. An exemplary light can comprise a lamp 37 having an illuminance of between 35,000 lux and 105,000 lux, or between 45,000 lux and 70,000 lux, or about 55,000 lux. In some embodiments, the lamp comprises Model 7 manufactured by Designs for Vision Inc, Bohemia, New York, USA. In some embodiments, the lamp comprises a Surgical LED 2.0 manufactured by SurgiTel® of Ann Arbor, Michigan, USA. In FIG. 1, a portion 123 of the light beam 114 from the lamp 37 and lens 113 passes through the facial shield 102, but another portion 121 is reflected at an angle from an internal surface 115 of the facial shield 102. See reflected light 114r in FIGS. 24-25. The reflection of a standard lamp, without the use of any mitigation, would be seen by the user and would distract the user's vision. However, the opaque flexible tongue 39 is configured to intercept the reflective beam of light 121, and not let it significantly pass through the opaque material of the flexible tongue 39. Thus, the flexible tongue 39 acts as a glare shield. The spot 118 that is shown on the upper surface 116 of the flexible tongue 39 is evidential of this effect. In FIG. 1, the lamp 37 is angled downward in relation to a horizontal axis. In FIG. 2, the lamp 37 has been adjusted so that the light beam 114 radiates almost perpendicularly to the facial shield 102. There is almost no reflection. The lamp 37 can be configured such that the light beam 114 has an intended distance to the primary external location or surface to be viewed of between about ten inches and about 24 inches, or between about ten inches and about 18 inches, or between about 12 inches and about 16 inches.

The flexible tongue 39 includes the upper surface 116 and a distal edge 117. As the angulation of the adjustable lamp holder 38 and lamp 37 (together) in relation to the horizontal is changed, a varying surface area of the upper surface 116, adjacent to the distal edge 117, interfaces with the internal surface 115 of the facial shield 102. The upper surface 116 of the flexible tongue 39 is configured to be slidable, up and down, in relation to the internal surface 115 of the facial shield 102. Thus, a portion of the upper surface 116 that is proximal to the contacting area of the upper surface 116 is in position to intercept the reflected light beam, thus not allowing it to travel into the user's visual sight and interfere with the user's vision and visual perception. The flexure of the flexible tongue 39 is configured to be predominantly within the elastic limit of the material of the flexible tongue 39 such that contact is maintained with at least a very distal portion of the upper surface 116 and the internal surface 115, or at very least the distal edge 117 and the internal surface 115. This also assures that the response of the flexible tongue 39 remains the same over multiple adjustments in the angulation of the adjustable lamp holder 38/lamp 37, e.g., up and down with many repetitions. In some embodiments, at least the upper surface 116 includes a matte finish, to further minimize any additional reflection of light beams. The width W of the flexible tongue 39 along the working section length WSL can be configured such that the maximum width (0.9 inches, or 0.75 inches, or 0.65 inches, for example) does not impede the field of vision of the user, at least over the working angle range of adjustment of the adjustable lamp holder 38/lamp 37. Alternative to the black opaque flexible tongue 39, a lighter color can be utilized, for example opaque white, if, for example, any glowing (e.g., firefly effect) is not significant such that it is bothersome to the user.

Figure 11:
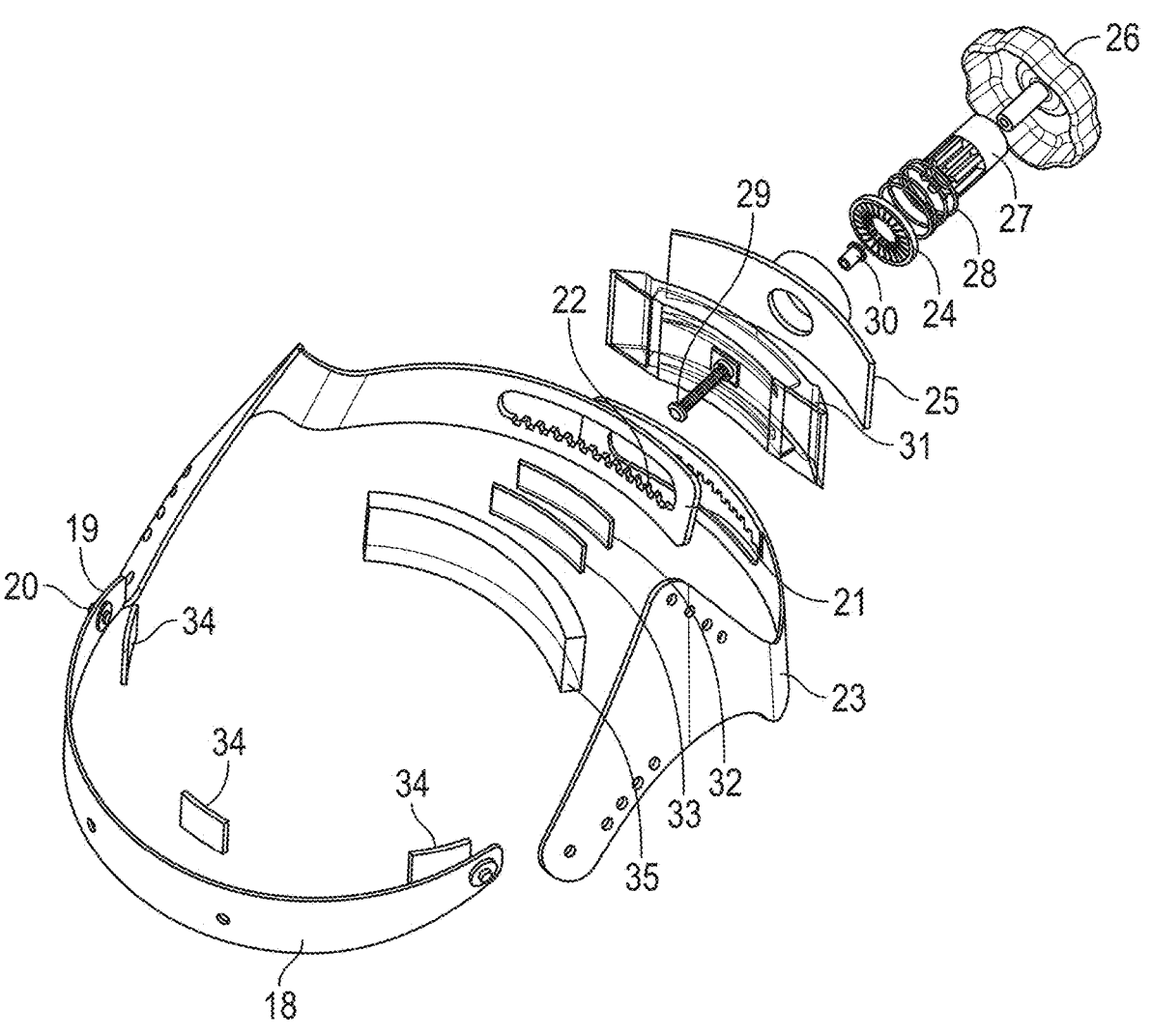
FIG. 11 is an exploded perspective view of a headband assembly of the personal protection system of FIG. 7, according to an embodiment of the present disclosure.

Turning to FIGS. 7-14, another embodiment of a personal protection system 1, utilizing the glare shield assembly 14 is illustrated. The following components are included:

Personal protection system 1; plastic liner 2; metal snap studs 3, 4; foam pads 5, 6 (which can comprise polyurethane foam or polyethylene foam); right side liner tab 7; left side linter tab 8; trapezoidal shaped curved foam pad 9 (which can comprise polyurethane foam or polyethylene foam); bracket 10; retaining screw 11; washer 12; nut 13; glare shield assembly 14; stop 15 (FIG. 13); helmet 16 (partially cut-away); spacer 17; headband front strap 18 (FIGS. 10-11); post/stud 19 (FIG. 11); snap 20 (FIG. 11); right headband side strap 21 (FIGS. 9-11); silicone lubrication 22 (FIG. 11); left headband side strap 23 (FIGS. 9-11); ratchet gear 24 (FIG. 11); ratchet cover 25 (FIG. 11); adjustment knob 26 (for circumferential size/tightness of headband) (FIGS. 7 and 9-11); adjustment knob gear 27 (FIG. 11); ratchet spring 28 (FIG. 11); screw 29 (torx head) (FIG. 11); eyelet 30 (FIG. 11); ratchet housing 31 (FIG. 11); Velcro strip with hooks 32 (FIG. 11); Velcro strip with loops 33 (FIG. 11); pads 34 (adhesive side in to headband/Velcro side out) (FIG. 11); and back cushioning pad 35 (foam) (FIG. 11).

The personal protection system 1 is similar to the personal protection system 100, but more detail is shown in relation to the adjustable headband 36 for placement on the user's head that acts as a support carried on the head 104 of a user 103. The headband 36 (FIG. 10) comprises the headband front strap 18, right headband side strap 21, left headband side strap 23, and adjustment knob 26, as well as other parts detailed in FIG. 11. The facial shield 102 (FIG. 1) is configured to be coupled to the support such that the facial shield 102 is maintained anterior to the head/face 104 of the user 103. In some embodiments, the support comprises the headband 36. In some embodiments the support comprises a helmet 16. In some embodiments, the support comprises the plastic liner 2. The facial shield 102 has substantial clarity for viewing therethrough, and further comprises an outer surface 119 and an inner surface 115. In some embodiments, the facial shield 102 comprises polycarbonate. The personal protection system 1 further comprises an emitted-light source (e.g., the lamp 37 and lens 113) configured to be carried between the facial shield 102 and the user 103 and configured to provide a light beam 114 that is able to at least partially radiate through the facial shield 102. The personal protection system 1 further comprises a flexible elongate opaque sheet (e.g., flexible tongue 39) having a first end coupled to the emitted-light source and a free second end configured to maintain contact with the inner surface 115 of the facial shield 102 as the light beam 114 from the lamp 37/lens 113 is angularly adjusted over a working adjustment angle range.

Figure 15A:
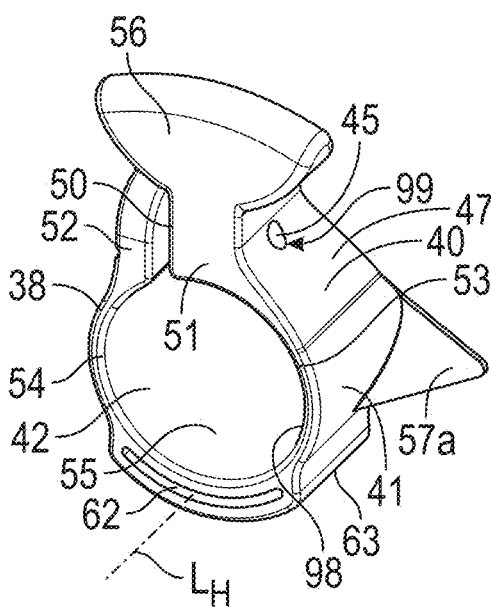
FIG. 15A is a perspective view of an adjustable lamp holder, according to an embodiment of the present disclosure.
Figure 15B:
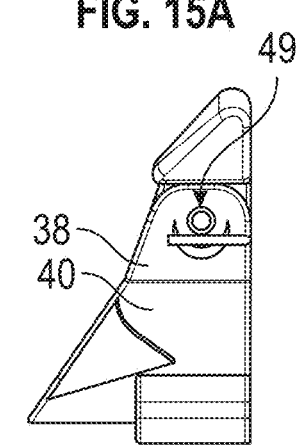
FIG. 15B is a side view of the adjustable lamp holder, according to an embodiment of the present disclosure.
Figure 15C:
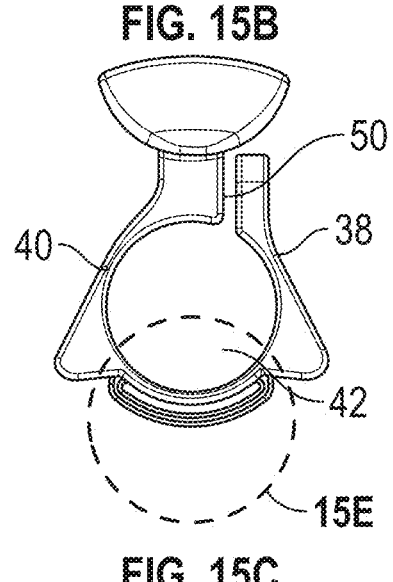
FIG. 15C is a front view of an adjustable lamp holder, according to an embodiment of the present disclosure.
Figure 15D:
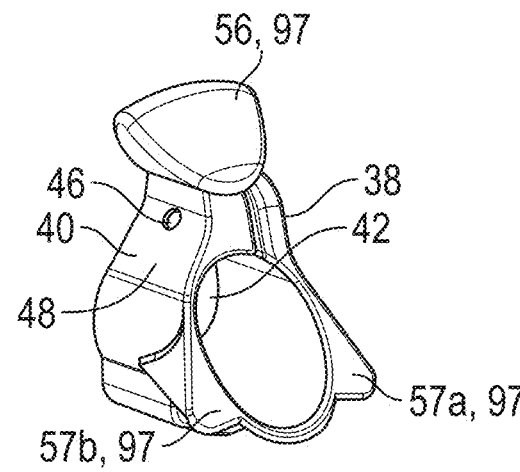
FIG. 15D is a perspective view of an adjustable lamp holder, according to an embodiment of the present disclosure.
Figure 15E:
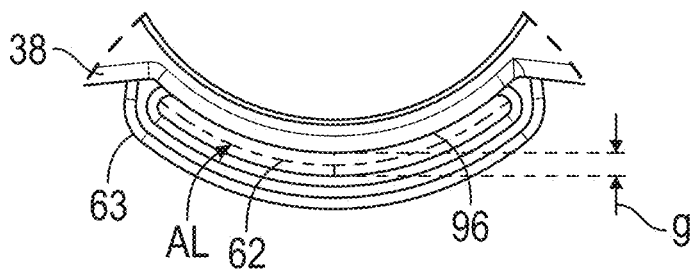
FIG. 15E is a detailed view of the adjustable lamp holder of FIG. 15C taken within circle 15E.
Figure 16A:
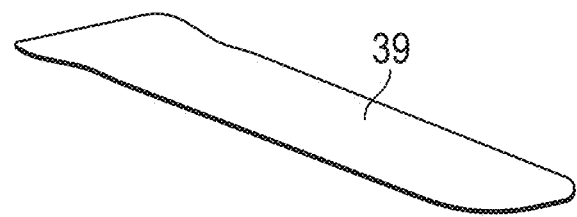
FIG. 16A is a perspective view of a flexible tongue, according to an embodiment of the present disclosure.
Figure 16B:
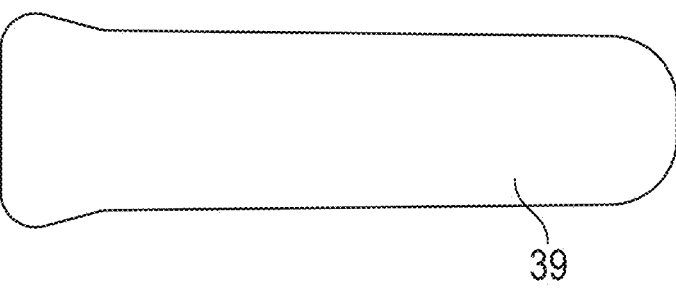
FIG. 16B is an elevation view of the flexible tongue, according to an embodiment of the present disclosure.
Figure 16C:
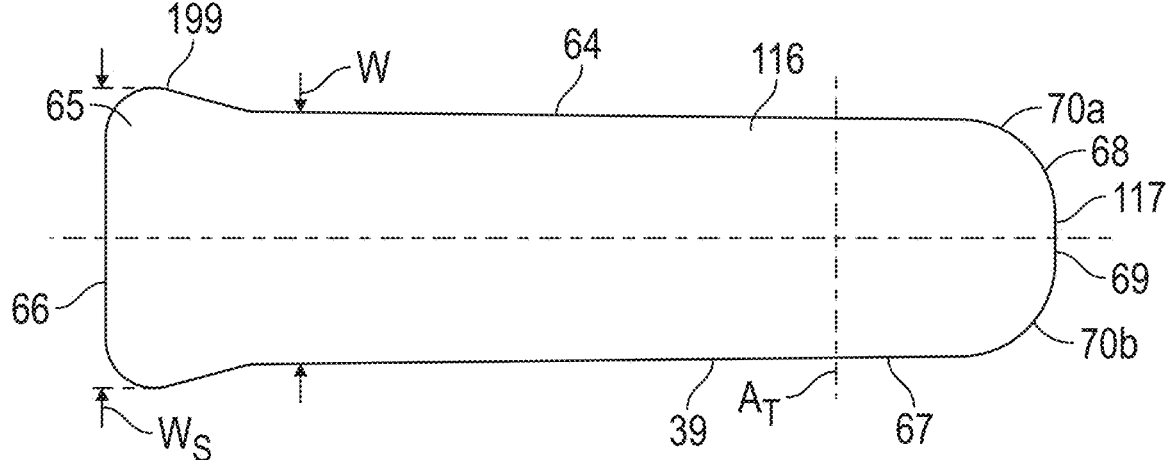
FIG. 16C is an elevation view of the flexible tongue, according to an embodiment of the present disclosure.
Figure 16D:
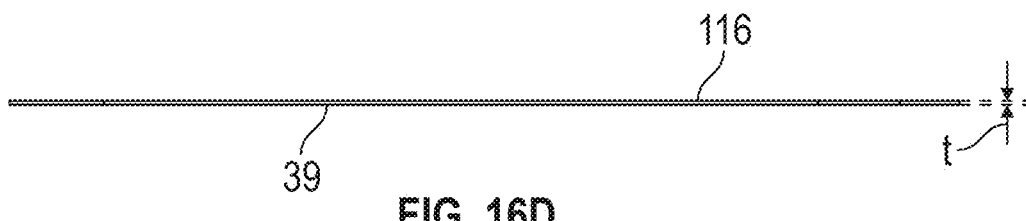
FIG. 16D is a side view of the flexible tongue, according to an embodiment of the present disclosure.

FIGS. 15A-19G illustrate components of the personal protection system 1 in a particular embodiment. The dimensions described represent only one or more possible embodiment. Other embodiments with other dimensions are contemplated, and are within the bounds of the disclosure. As shown in FIGS. 15A-15E, the adjustable lamp holder 38 comprises a housing 40 comprising polycarbonate, or another rigid material. In some embodiments, the housing 40 is a black color, to absorb light and to minimize additional reflection of light (e.g by its surface). The housing 40 comprises contoured outer surfaces 41 and a cylindrical channel 42 passing through the housing 40. The cylindrical channel 42 has an inner diameter that is configured to allow the close sliding placement and engagement of an outer cylindrical surface 43 (FIG. 3) of a lamp housing 44 of the lamp 37. A hole 45 in a left side 47 of the housing 40 and a hole 46 in a right side 48 of the housing 40 each allow the passage of a tightening screw 49 (FIGS. 5, 15B, and 23-27). One or both of the holes 45, 46 can comprise an internal thread 99 for interfacing with an external thread (not shown) of the tightening screw 49. The housing 40 includes an elongate gap 50 between a central thickened portion 51 and a side wall 52 (FIG. 15A). The housing 40 contains some flexure/plastic deformability at least in a left thinned arc 53 and a right thinned arc 54, the arcs 53, 54 defining some of the circumference of the housing 40 that surrounds the channel 42. The amount of flexing of the arcs 53, 54 is controlled by changing the amount of the gap 50, via tightening or loosening of the screw 49. Thus, the tightening of the tightening screw 49 causes flexure in one or both of the left thinned arc 53 and the right thinned arc 54 and allows the gap 50 to decrease as the side wall 52 is brought toward the central thickened portion 51. This allows an internal circumference 98 of the cylindrical channel 42 to decrease and allows an inner surface 55 of the cylindrical channel 42 to grip the outer cylindrical surface 43 of the lamp housing 44. The tightening screw 49 can be tightened to a desired tightening torque to grip the lamp housing 44 and to statically maintain the axial and radial position of the lamp 37 in relation to the housing 40.

The housing 40 includes an upper contact surface 56 and a lower contact surface 57. The lower contact surface 57 comprises a left lower contact surface 57a and a right lower contact surface 57b. The contact surfaces 56, 57a, 57b together represent sub-surfaces of a combined contact surface 97. The contact surfaces 56, 57 are configured to allow adjustment of the amount of angulation of the adjustable lamp holder 38 (and thus of the lamp 37 and of the light beam 114) via contact and applied force (e.g., fingertip(s), finger pad/pulp(s), or knuckle(s)) by a user or another personnel. The contact can be direct onto one or more of the surfaces 56, 57a, 57b if the facial shield 102 is not in place; or, the contact can be indirectly applied via pressure applied via directly by the user to an external surface 168 of the facial shield, as will be described further in relation to FIGS. 26-27. As shown in FIGS. 5, 12, and 23-27, a pivot joint 58 (or pivot) comprising a tightening screw 59 couples the housing 40 to the bracket 10. The bracket 10 attaches to the liner 2 and the spacer 17 via retaining screws 11, washers 12, and nuts 13, a shown in FIGS. 7 and 9. The bracket 10 has a curve that is concave on an interior 60 (FIG. 13) and convex on an exterior 61 (FIG. 12) to conform to the shape of the liner 2. In some embodiments, the bracket 10 is produced from a flat sheet, as shown in FIG. 17B, and then cold-formed or heat-formed into a curved shape, as shown in FIG. 17C. The curve of the bracket 10 generally has a radius of curvature that is somewhat larger than the radius of curvature of the anterior portion of the head of the user. In some embodiments the radius of curvature is two inches to four inches, or 2.5 inches to 3.5 inches, or 2.75 inches to 3.25 inches. Generally, while the user wears the personal protection system 1, pressure applied to the upper contact surface 56 (FIG. 26), e.g., by contacting an adjacent outer portion 167 of the facial shield 102 with one or more finger, causes the adjustable lamp holder 38/lamp 37/light beam 114 to be rotated upwardly, such that the light beam 114 is oriented (superiorly) toward a higher elevation target. Generally, pressure applied to one or both of the lower contact surfaces 57a, 57b (FIG. 27), e.g., by contacting an adjacent outer portion 169 of the facial shield 102 with one or more finger, causes the adjustable lamp holder 38/lamp 37/light beam 114 to be rotated downwardly, such that the light beam 114 is oriented (inferiorly) toward a lower elevation target. The displaceable material of the facial shield 102 also includes memory, to return to its shape (e.g., concave on the inside) after the applied pressure is removed, by removing the finger/hand. In other embodiments, the facial shield 102 can include at least some plastic deformation, so that the shape of the facial shield 102 changes at least a little during adjustments of the lamp 37. The tightening screw 59 is configured to adjust the amount of rotational resistance in the pivot joint 58 via the tightening of the tightening screw 59 to an appropriate tightening torque. The tightening torque or torque range can be chosen such that the pushing force applied by (and felt by) the user or other personnel (e.g., on a contact surface 56, 57a, 57b) is low enough to be easily achieved, but high enough so that it is not accidentally achieved from light, inadvertent contact. The pushing force is related to the moment arm from the point of (e.g., indirect) contact on the contact surface 56, 57a, 57b to the pivot joint 58 axis, and the moment of this moment arm is related to the tightening torque. In FIG. 26, this is represented by moment arm $MA_1$, and in FIG. 27 it is represented by moment arm $MA_2$. The finger contact to the outside of the facial shield 102, adjacent to one of the contact surfaces 56, 57a, 57b, can be by a gloved finger or an ungloved finger. It can also be by a scrubbed (e.g., substantially sterile) finger or by a non-sterile finger, depending on the procedure being performed. In some embodiments, the contact surface 56 comprises a central substantially triangular tab, and the contact surfaces 57a, 57b comprise left and right substantially triangular tabs. The contact surfaces 56, 57a, 57b can each comprise a concave surface. The surface area of the contact surfaces 56, 57a, 57b can each range from about 0.02 $in_2$ to about 0.80 $in_2$, or about 0.04 $in_2$ to about 0.65 $in_2$.

In some embodiments, the rotational resistance of the pivot joint 58 is set (e.g., factory preset) or adjusted (e.g., by the user) to a value ranging from 0.2 lbf·in to 5.0 lbf·in. In some embodiments, the rotational resistance of the pivot joint 58 is set or adjusted to a value ranging from 1.0 lbf·in to 5.0 lbf·in. In some embodiments, the rotational resistance of the pivot joint 58 is set or adjusted to a value ranging from 2.0 lbf·in to 3.0 lbf·in. In some embodiments, the tightening torque of the tightening screw of the pivot joint 58 is set or adjusted to a value ranging from 0.2 lbf·in to 5.0 lbf·in. In some embodiments, the tightening torque of the tightening screw of the pivot joint 58 is set or adjusted to a value ranging from 1.0 lbf·in to 5.0 lbf·in. In some embodiments, the tightening torque of the tightening screw of the pivot joint 58 is set or adjusted to a value ranging from 2.0 lbf·in to 3.0 lbf·in. In some embodiments, a minimum force (e.g., normal force) applied to the contact surface 56 to cause the rotation of the pivot joint 58 is between 0.1 lb. and 2.0 lb. In some embodiments, a minimum force (e.g., normal force) applied to the contact surface 56 to cause the rotation of the pivot joint 58 is between 0.5 lb. and 1.5 lb. In some embodiments, a minimum force (e.g., normal force) applied to the contact surface 56 to cause the rotation of the pivot joint 58 is between 0.75 lb. and 1.25 lb. In some embodiments, a minimum force (e.g., normal force) applied to the contact surface 57a to cause the rotation of the pivot joint 58 is between 0.1 lb. and 2.0 lb. In some embodiments, a minimum force (e.g., normal force) applied to the contact surface 57a to cause the rotation of the pivot joint 58 is between 0.5 lb. and 1.5 lb. In some embodiments, a minimum force (e.g., normal force) applied to the contact surface 57b to cause the rotation of the pivot joint 58 is between 0.75 lb. and 1.25 lb. In some embodiments, a minimum force (e.g., normal force) applied to the contact surface 57b to cause the rotation of the pivot joint 58 is between 0.5 lb. and 1.5 lb. In some embodiments, a minimum force (e.g., normal force) applied to the contact surface 57b to cause the rotation of the pivot joint 58 is between 0.75 lb. and 1.25 lb. In some embodiments, a minimum force (e.g., normal force) applied via simultaneous contact to the contact surfaces 57a, 57b (e.g., by two separate fingers) to cause the rotation of the pivot joint 58 is between 0.1 lb. and 2.0 lb. In some embodiments, a minimum force (e.g., normal force) applied via simultaneous contact to the contact surfaces 57a, 57b to cause the rotation of the pivot joint 58 is between 0.5 lb. and 1.5 lb. In some embodiments, a minimum force (e.g., normal force) applied via simultaneous contact to the contact surfaces 57a, 57b to cause the rotation of the pivot joint 58 is between 0.75 lb. and 1.25 lb.

The housing 40 further comprises an arc-shaped cavity 62 extending through a lower portion 63. The cavity 62 has a bilateral, substantially transversely extending arc having an arc length AL that is larger than a maximum width W (FIG. 16C) of the flexible tongue 39. The arc length AL can be between about 0.25 inch and about 1.5 inch, or between about 0.5 inch and about 0.8 inch. The arc-shaped cavity is curved in relation to a cavity longitudinal axis LH. The cavity 62 has a gap g that is larger than a thickness t (FIG. 16D) of the flexible tongue 39. Thus, the flexible tongue 39 is configured to slide longitudinally within the cavity 62, and the cavity 62 is configured to place the flexible tongue 62 into a slightly curved shape (e.g., a flower petal shape that is in relation to a tongue longitudinal axis LT). The curved shaped of the flexible tongue 62 can cause an increase in the bulk bending stiffness of the flexible tongue 39 in relation to a transverse axis Ar. In some embodiments, the cavity 62 has an arc length that is slightly larger than a maximum width W of the flexible tongue 39, and the cavity 62 has a gap g that is slightly larger than a thickness t of the flexible tongue 39. Thus, the flexible tongue 39 is capable of being slid back-and-forth within the cavity 62, but the cavity 62 provides stability, such that the flexible tongue 39 has some resistance, and maintains a generally longitudinal extension direction. The additional friction caused by increased contact and increased normal forces between the flexible tongue 39 and the interior surfaces 96 serve to stabilize and maintain the position of the flexible tongue 39 in relation to the housing 40 when not being adjusted.

Figures 20, 21, 22:
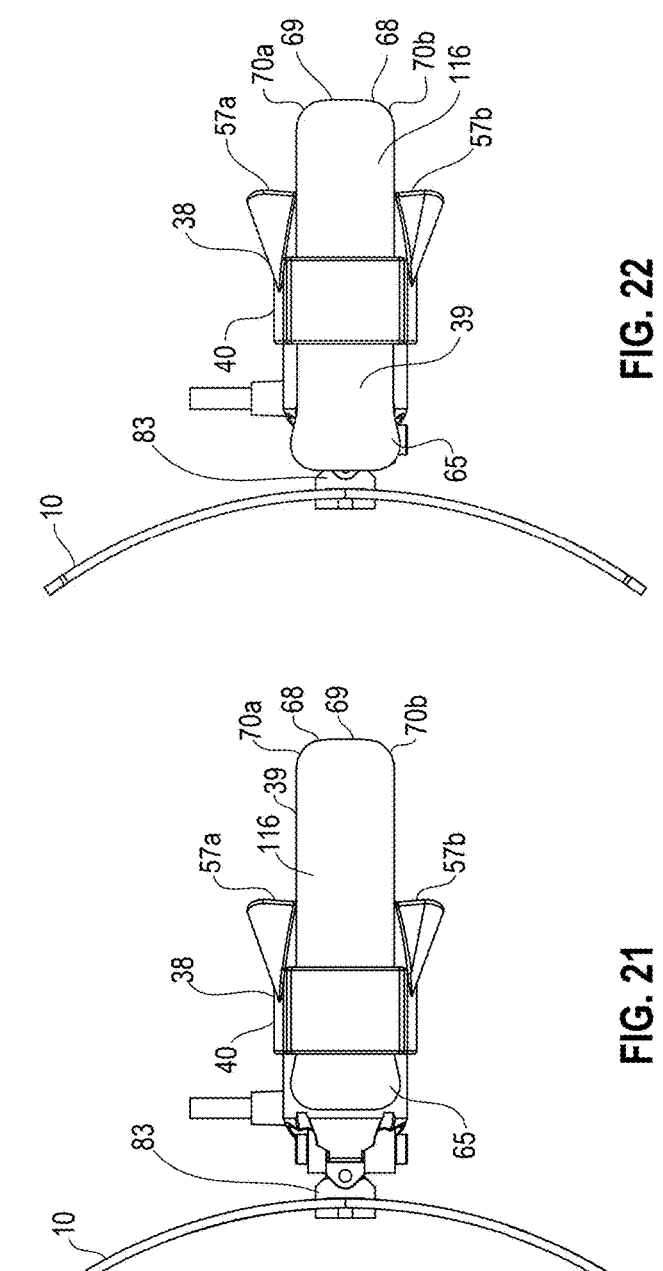
FIG. 20 is a front view of an adjustable lamp and glare shield assembly, according to an embodiment of the present disclosure.
FIG. 21 is a bottom view of the adjustable lamp and glare shield assembly of FIG. 20 with a first glare shield extension amount.
FIG. 22 is a bottom view of the adjustable lamp and glare shield assembly of FIG. 20 with a second glare shield extension amount.

The flexible tongue 39 further comprises a working section 64 that is configured to be slid through the cavity 62, and a stop 65 at a first end 66 of the flexible tongue 39, the stop 65 having a maximum width $W_s$ that is greater than the arclength AL of the cavity 62. Thus, the flexible tongue 39 can be adjusted longitudinally to a desired configuration (FIGS. 21 and 22). However, the stop 65 keeps the flexible tongue 39 from being removed from the cavity 62 as it is extended (arrow, FIG. 16C) to a maximum position, wherein the stop 65 abuts the lower portion 63 at the maximum width $W_s$, or at a portion of the flexible tongue 39 that is between the maximum width $W_s$ and the working section 64 (see FIG. 21). The abutment occurs when a portion of the flexible tongue 39 along a width increase portion (e.g., taper) 199 is identical or just slightly larger than the arc length AL of the cavity 62. A distal portion 67 of the flexible tongue 39 includes a distal end 68 having a distal edge 117 comprising a flat portion 69, and fillets 70a, 70b, each laterally adjacent to the flat portion 69 and extending from the flat portion 69. The flat portion 69 adds stability to the alignment of the flexible tongue 39 in relation to the inner surface 115 of the facial shield 102 as the flexible tongue 39 is flexed and as it slides up or down in relation to the inner surface 115. The flat portion 69 can comprise a flat, straight, transverse edge. FIG. 21 illustrates the flexible tongue 39 adjusted with close to the maximum amount of extension in relation to the housing 40. FIG. 22 illustrates the flexible tongue 39 in a partially retracted position in relation to the housing 40. The curving of the flat flexible tongue 39 working section 64 within the arc-shape of the cavity 62 can be configured to add a particular amount of friction to maintain the chosen longitudinal position of the flexible tongue 39, but still allowing for user manipulation and adjustment of the amount of longitudinal extension. In some embodiments, a certain amount of extension of the flexible tongue 39 (less than maximum) allows the arc-shaped cavity 62 to cause the entirety of the flexible tongue 39 that is distal to the cavity 62 to be held in a curved shape, whereas a maximum amount of extension curves some of the flexible tongue 39, but not an extreme distal section of the flexible tongue 39, which remains substantially flat (e.g., overall flower petal shape 125, FIG. 14). Thus, the longitudinal adjustment not only can control the amount of the flexible tongue 39 that interfaces with the inner surface 115 of the facial shield 102, but also can control the shape at the distal portion 67 of the flexible tongue 39. The control of the shape of the distal portion can also be used to affect how the distal portion 67 interfaces with the inner surface 115 of the facial shield 102.

In some embodiments, the lamp 37 incorporates optical vignetting to gradually decrease in light intensity towards the image periphery. Thus, the light beam 114 can be somewhat controlled to diverge less than in a standard lamp. For this reason, the distal section of the flexible tongue 39 need not increase in width toward the distal tip. In an alternative embodiment, however, shown in FIG. 35, a flexible tongue 39' can be configured with a divergent (increasing width) distal section 162, to allow the absorption of any of the light beam 114 that does diverge. The distal section includes a width increase portion 198, that can comprise a taper on each side, like the width increase portion 199. The cavity 62 and the housing 40 allow the flexible tongue 39 to be adjusted to the appropriate amount of longitudinal extension (e.g., extended length) so that the distal portion 67 of the flexible tongue interferes (spatially) with the path of reflected light, thus attenuating reflection and its effect. This utility allows a significantly high intensity lamp to be utilized within the small space behind the facial shield 102, wherein the lamp is quite close to the user's eyes.

In some embodiments, the working section 64 has a working section width W that is about the same or is slightly wider than the arc length AL of the cavity 62 (or of a transverse horizontal width of the cavity 62, if the cavity extends in a substantially planar manner). Thus, when the working section 64 is slid longitudinally within the cavity 62, an interference from the lateral edges of the flexible tongue 39 at the working section 64 against the outer edges of the cavity 62 causes some frictional resistance between the flexible tongue 39 and the housing 64 so that the longitudinal movement is not so easy that it is unacceptably too easy. The flexible tongue 39 is thus held sufficiently in place when not being forcibly moved, e.g., by the user. In other embodiments, the working section 64 has a working section thickness (e.g., the thickness t of the flexible tongue 39) that is substantially the same, or even slightly larger than a gap g in the cavity 62, such that additional friction is added by this interface, and additional control of extension and retraction of the tongue 39, and/or stability of the tongue 39 in relation to the housing 40 when not being adjusted, and during use. In some embodiments, the amount of friction between the flexible tongue 39 and the housing 40 (via the cavity 62) can be controlled by the width W of the working section 64 and the thickness t of the working section, and their relation to the arc length AL and gap thickness g of the cavity 62. If the edges of the cavity 62 are radiused, and if the edges of the flexible tongue 39 are squared, then the fit can include the longitudinally extending vertices of the square cross-section of the flexible tongue 39 forces against the radiused ends of the cavity 62.

Figure 12:
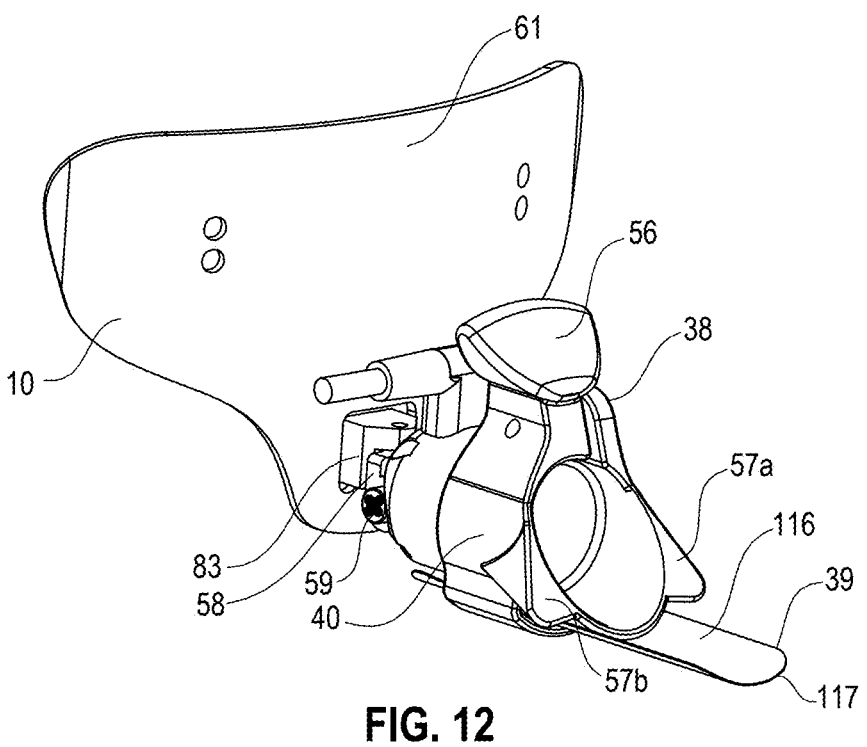
FIG. 12 is a first perspective view of an aimable lamp holder and glare shield assembly of the personal protection system of FIG. 7, according to an embodiment of the present disclosure.
Figure 13:
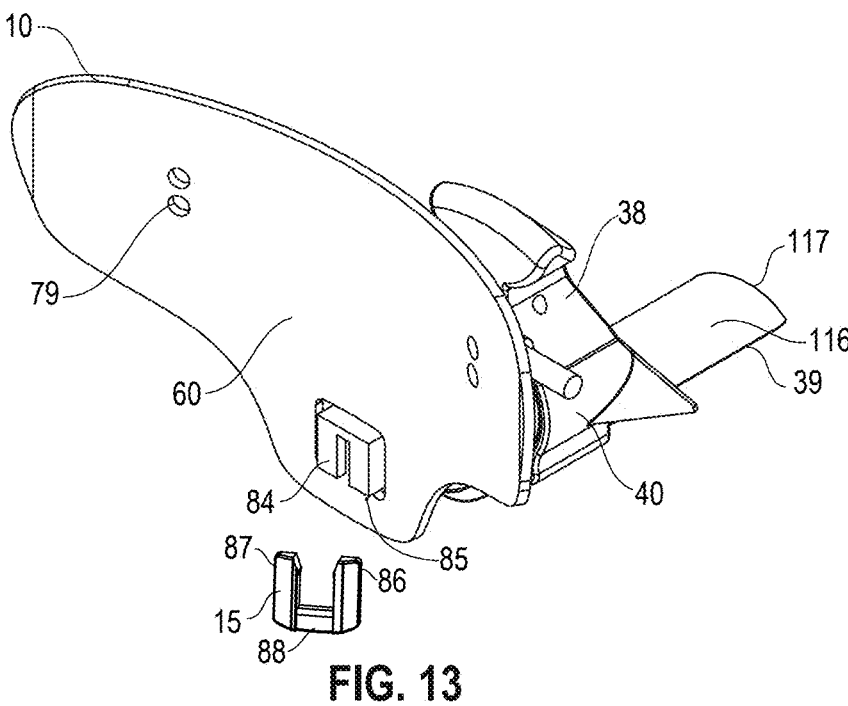
FIG. 13 is a partially-exploded second perspective view of the aimable lamp holder and glare shield assembly of FIG. 12, according to an embodiment of the present disclosure.
Figure 14:
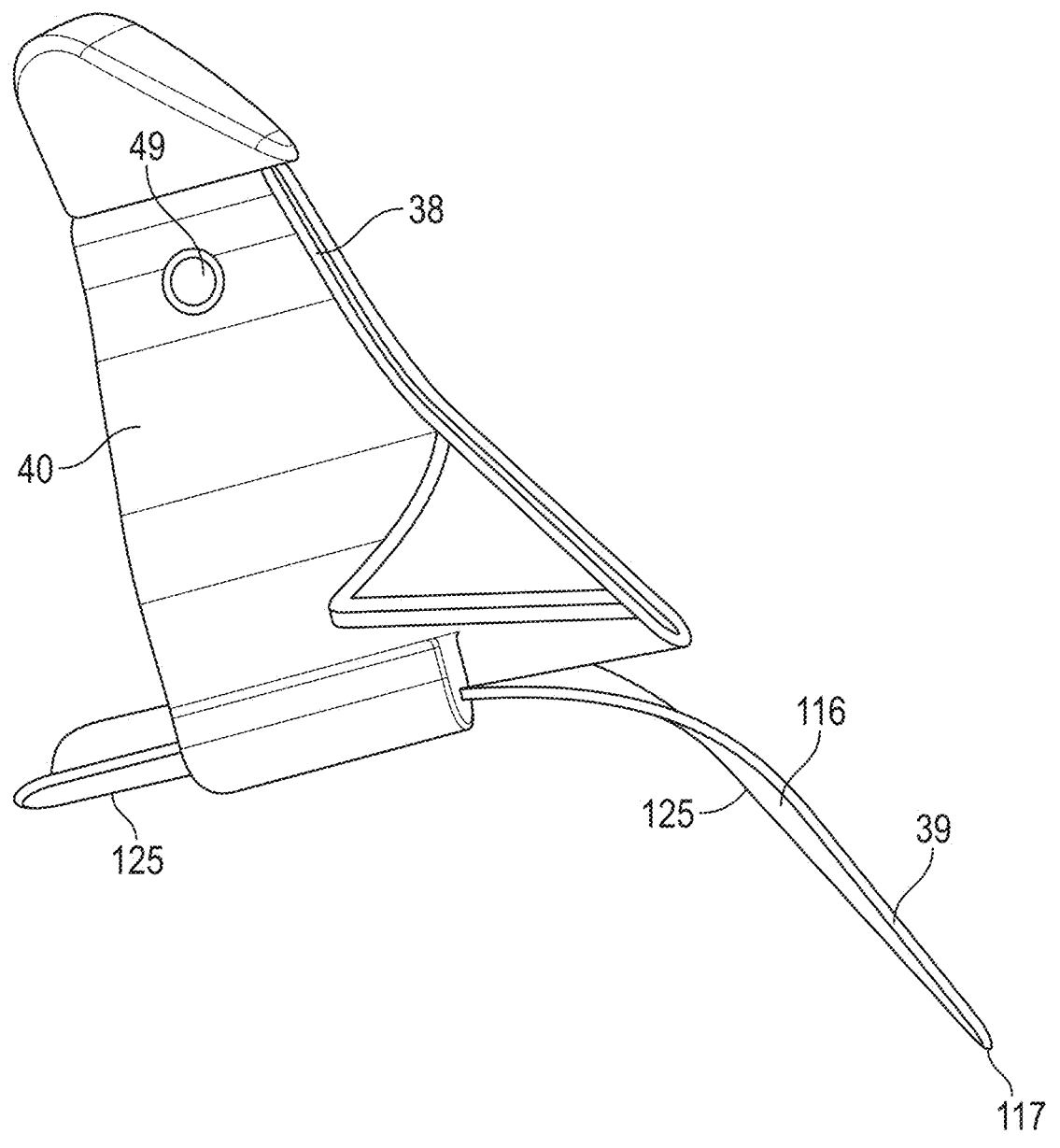
FIG. 14 is a side view of the aimable lamp holder and glare shield assembly of FIG. 12, according to an embodiment of the present disclosure.
Figure 17A:
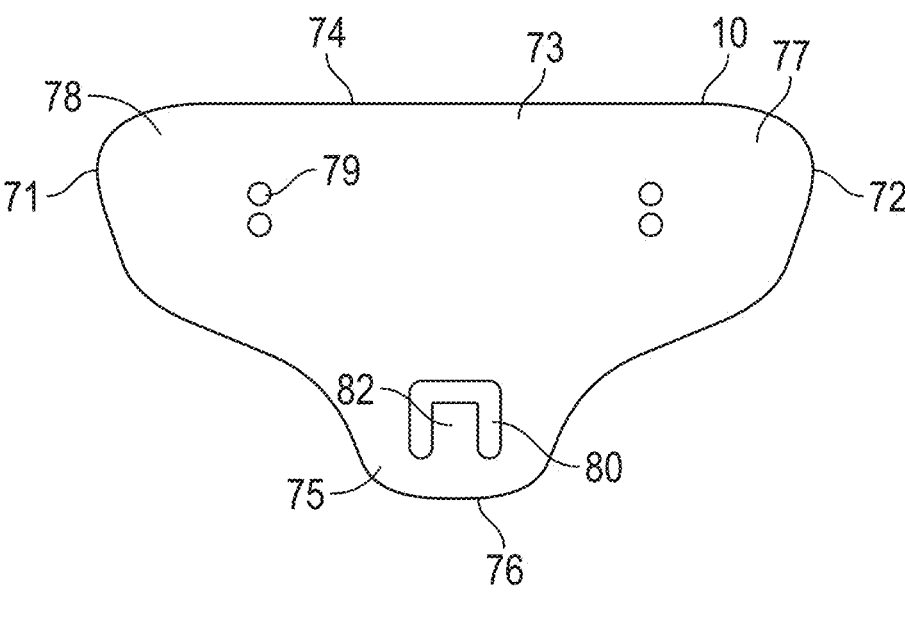
FIG. 17A is an elevation view of a bracket, according to an embodiment of the present disclosure.
Figure 17B:
FIG. 17B is a side view of the bracket, according to an embodiment of the present disclosure.
Figure 17C:
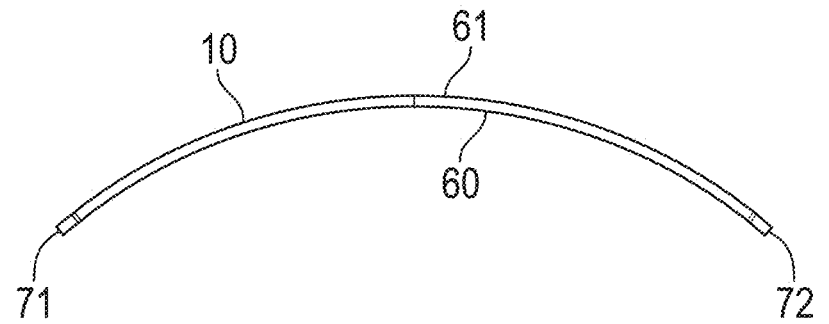
FIG. 17C is three-dimensional view of the bracket, according to an embodiment of the present disclosure.
Figures 18A, 18B, 18C, 18D:
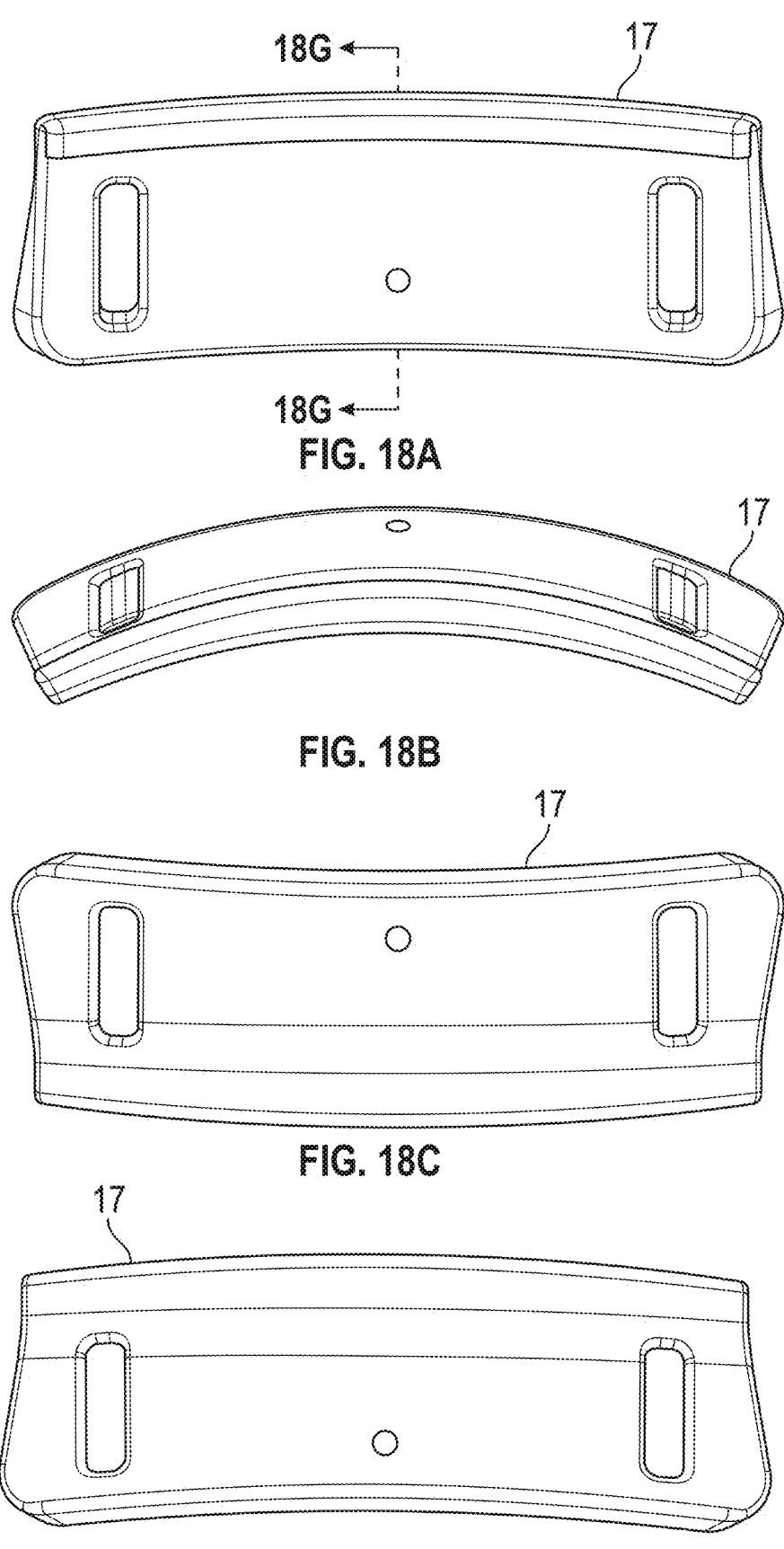
FIG. 18A is a perspective view of a spacer, according to an embodiment of the present disclosure.
FIG. 18B is a perspective view of the spacer of FIG. 18A, according to an embodiment of the present disclosure.
FIG. 18C is a perspective view of the spacer of FIG. 18A, according to an embodiment of the present disclosure.
FIG. 18D is a perspective view of the spacer of FIG. 18A, according to an embodiment of the present disclosure.
Figures 18E, 18F, 18G, 18H, 18I:
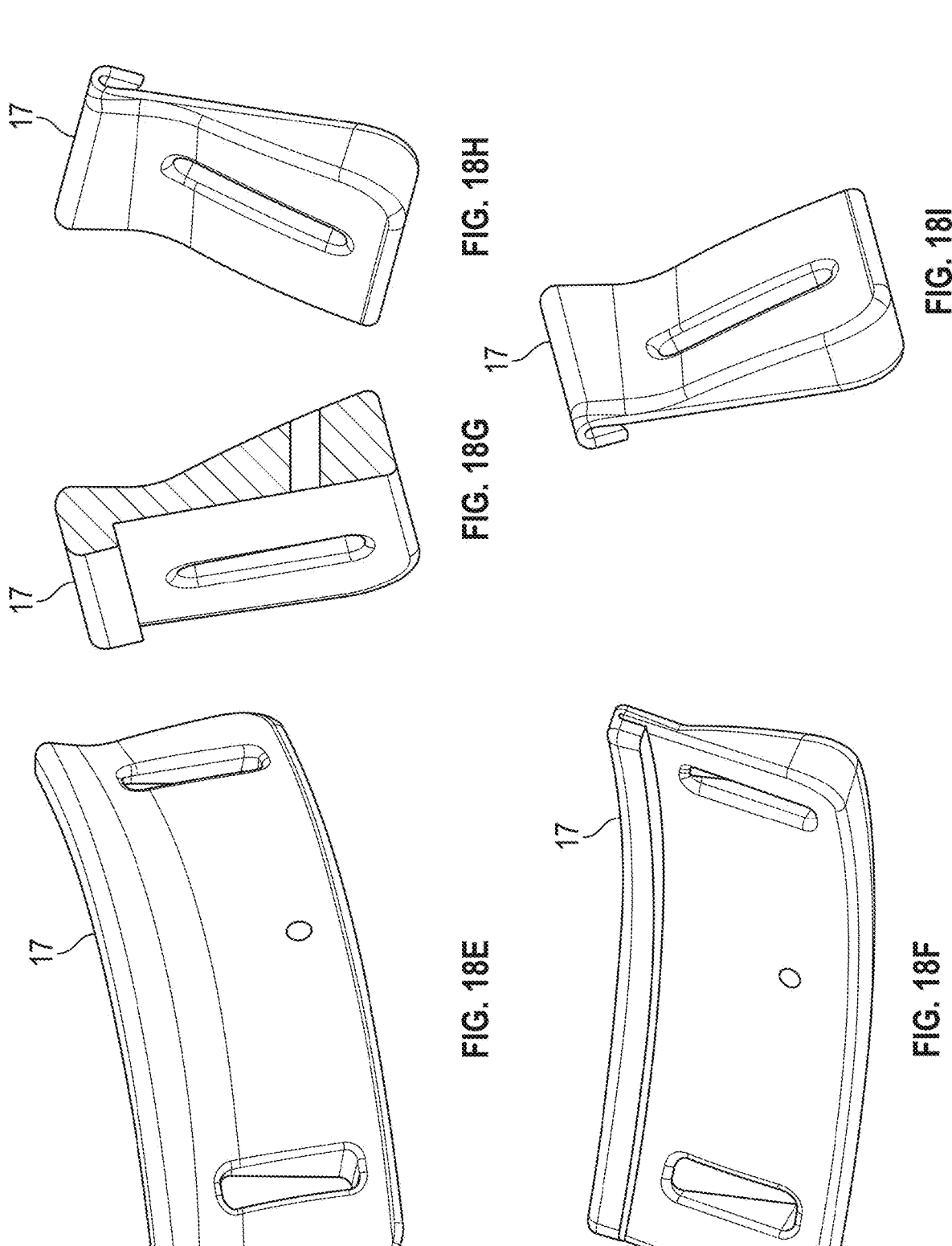
FIG. 18E is a perspective view of the spacer of FIG. 18A, according to an embodiment of the present disclosure.
FIG. 18F is a perspective view of the spacer of FIG. 18A, according to an embodiment of the present disclosure.
FIG. 18G is a cross-sectional view of the spacer of FIG. 18A, according to an embodiment of the present disclosure.
FIG. 18H is a perspective view of the spacer of FIG. 18A, according to an embodiment of the present disclosure.
FIG. 18I is a perspective view of the spacer of FIG. 18A, according to an embodiment of the present disclosure.
Figures 19E, 19F, 19G:
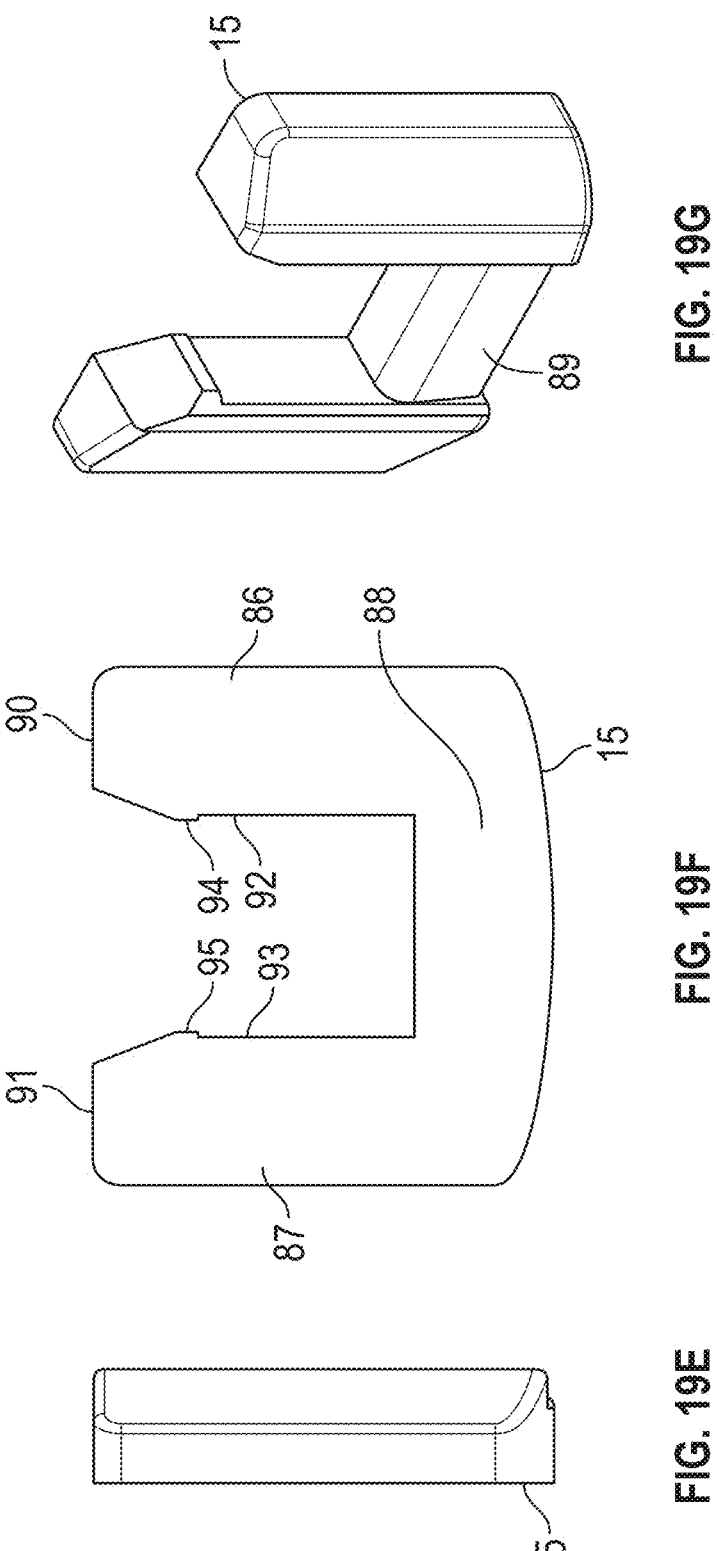
FIG. 19E is a third side view of the stop, according to an embodiment of the present disclosure.
FIG. 19F is second elevation view of the stop, according to an embodiment of the present disclosure.
FIG. 19G is a perspective view of the stop, according to an embodiment of the present disclosure.

Turning to FIGS. 17A-17C, the bracket 10 comprises a first end 71, a second end 72, an upper portion 73 having an upper edge 74, and a lower portion 75 having a lower edge 76. The upper portion 73 extends laterally in a left wing 77 and a right wing 78. The upper portion 73 includes holes 79 (e.g., four holes, as shown) for the retaining screws 11 to pass through. The lower portion 75 comprises a flat arch-shaped or C-shaped (rotated 90° in FIG. 17A) cutout 80 passing through the thickness 81 of the bracket 10, and defining a vertically upward pointing projection 82, or peninsula. The bracket 10 can be produced from a sheet of polymeric material, such as polycarbonate. The thickness of the sheet, and thus the thickness of the bracket 10 can be between about 0.035 inch and about 0.085 inch, or about 0.050 inch and about 0.070 inch. In some embodiments, the bracket 10 can be produced in a flat configuration (FIGS. 17A-B) by stamping, die-cutting, water jet cutting, laser cutting, or scoring. The bracket 10 can then be formed into a curved configuration (FIG. 17C), or can simply be assembled such that it is held in the curved configuration. As shown in FIGS. 12-13, housing 40 of the adjustable lamp holder 38 comprises a proximal portion 83 comprising a hollow clip 84 having an open internal cavity 85 configured to snap onto the projection 82 of the bracket 10. As shown in FIGS. 13 and 19A-19G, the stop 15 then is snapped into the cavity 85 of the clip 84, forcing the locking the projection 82 and the clip 84 in place in static relation to each other. The stop 15 is removable, and the projection 82/clip 84 are detachable from each other. The stop 15 comprises a U-shape (or C-shape) having a first leg 86, a second leg 87, and a central cross bar 88 connecting them together. The cross bar 88 has a lower front-to-back thickness than do the legs 86, 87, thus creating an undercut 89. The undercut 89 can be on a single side, or on both sides. The free ends 90, 91 of the legs 86, 87 include internal undercuts 92, 93 and barbs 94, 95 between the undercuts 92, 93 and the free ends 90, 91 to aid in the locking retention when snapped into place. Two tapered internal lead-ins 196, 197 taper inwardly to the barbs 94, 95 to facilitate snapping of the stop 15 against the internal contours of the hollow clip 84 within the internal cavity 95. The undercut 89 allows easy access to grip the cross bar 88 and pull the stop 15, when unsnapping and removing the stop 15 from the internal cavity 85 of the hollow clip 84.

As shown in FIGS. 7 and 18A-18I, the spacer 17 is assembled between the inner portion of the liner 2 and the exterior 61 of the bracket 10 so that the projection 82 is controlled to have a location in relation to the liner 2 that is somewhat inward. In various embodiments, different thicknesses of spacers 17 can be utilized to locate the housing 40 of the adjustable lamp holder 38 appropriately in relation to the facial shield 102, thus either closer to the user 103 or closer to the facial shield 102. The spacer 17 is molded, machined, 3D-printed, or produced by one or more various methods of additive manufacturing and/or subtractive manufacturing. The spacer 17 is a rigid part, and can be produced by a polymeric material such as polycarbonate. As shown best in FIG. 18B, the spacer 17 is curved and has a radius of curvature that matches that of the bracket 10, e.g., two inches to four inches, or 2.5 inches to 3.5 inches, or 2.75 inches to 3.25 inches.

Figure 23:
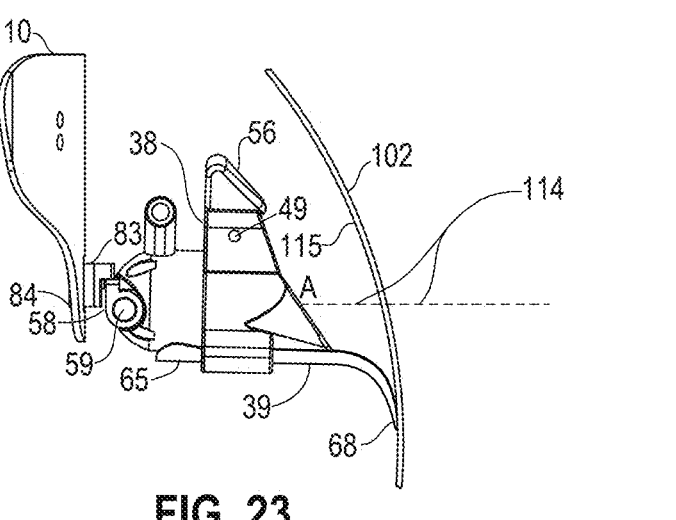
FIG. 23 is a side view of the adjustable lamp and glare shield assembly of FIG. 20 in a first adjustment state.

FIG. 23 illustrates the housing 40 in a somewhat horizontal position in relation to the facial shield 102, with the personal protection system 1 assembled. The user 103 presses on a portion 167 of the external surface 168 of the facial shield 102 to move it against the contact surface 56. The resulting pressure on the contact surface 56 from the inner surface 115 of the facial shield 102, as shown in FIG. 26, rotates the housing 40 about the pivot joint 58 toward one or more upward positions, such as the upward position shown in FIG. 25. The user 103 then presses on a one or more portion 169 of the external surface 168 of the facial shield 102 to move it against one or more contact surface 57. The resulting pressure on one or both of the contact surfaces 57a, 57b from the inner surface 115 of the facial shield 102, as shown in FIG. 27, rotates the housing 40 about the pivot joint 58 toward one or more downward positions, such as the downward position shown in FIG. 24. As shown in FIG. 26, indirect tactile pressure on the contact surface 56 occurs as a result of direct contact from the inner surface 115 of the facial shield 102, caused by direct tactile contact on the portion 167 of the external surface 168 of the facial shield 102 that overlies the contact surface 56. As shown in FIG. 27, indirect tactile pressure on the contact surface 57b occurs as a result of direct contact from the inner surface 115 of the facial shield 102, caused by direct tactile contact on the portion 169 of the external surface 168 of the facial shield 102 that overlies the contact surface 57b. This is also similar for the contact surface 57a. The variable flexure of the flexible tongue 39 as the upper surface 116 is slid against the inner surface 115 of the facial shield 102 maintains the desired amount of interface of the flexible tongue 39 and the inner surface 115 over the entirety of the working angular range of the pivot joint 58. The flexible tongue 39 is thus maintained in an effective position in relation to the light beam 114 to significantly intercept internal reflections off of the facial shield 102, such that the light beam 114 and facial shield 102 cannot produce a bothersome reflection into the eyes of the user 103. Furthermore, the flexible tongue 39 does not have to be modified or cut to different lengths or widths, once it is adjusted to a desired extension length (e.g., for the particular user face or head size or shape or for a particular headgear arrangement). The location of the flexible tongue 39 inside the protected space behind the facial shield 102 serves to protect it from the outside environment, keeping it clean and unsoiled, and where and when applicable, keeping it sterile. The flexible tongue 39 and the housing 40 are further protected from inadvertent bumping or other disruption from people or objects in the outside environment, while still remaining capable of being adjusted without requiring any removal of the headgear, including any removal of the facial shield 102.

Figure 24:
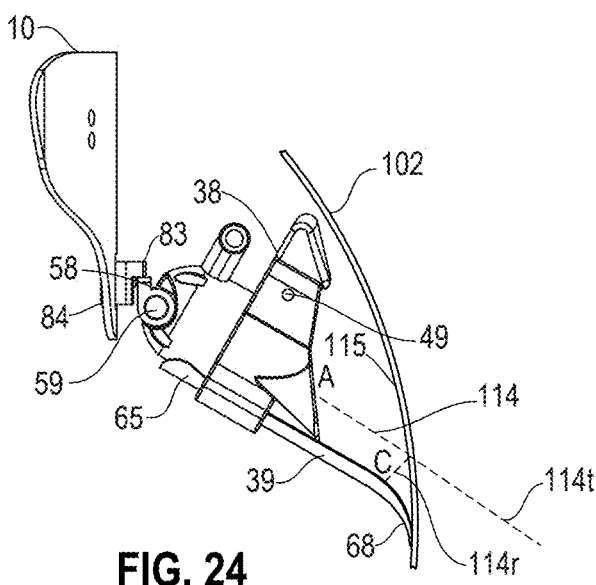
FIG. 24 is a side view of the adjustable lamp and glare shield assembly of FIG. 20 in a second adjustment state.
Figure 25:
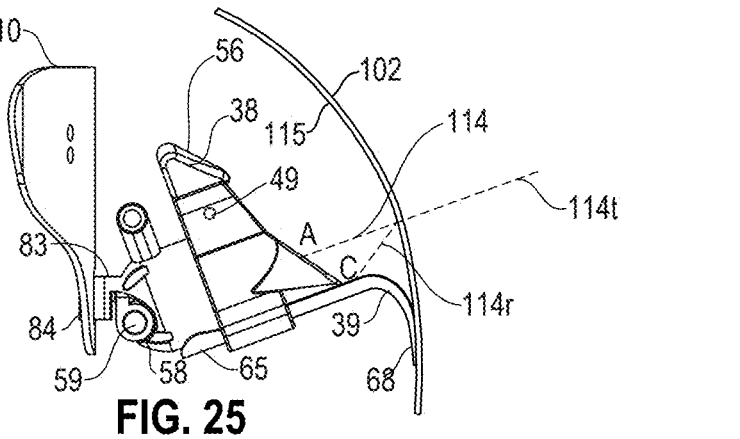
FIG. 25 is a side view of the adjustable lamp and glare shield assembly of FIG. 20 in a third adjustment state.

In FIG. 23, the light beam 114 is transmitted at an angle and with other conditions (facial shield 102 clarity, facial shield 102 thickness, facial shield 102 material, etc.) wherein there is little or no reflection from the inner surface 115 of the facial shield 102. The light beam 114 is substantially transmitted out of the lamp 37 (area A) toward the target viewing area B. In FIGS. 24 and 25, some of the light beam 114 is transmitted through the facial shield 102 (transmitted light 114t) toward the viewing area B, and some of the light beam 114 is reflected off the facial shield 102 (reflected light 114r) at the inner surface 115 at an angle and is substantially absorbed by the flexible tongue 39 at area C. Thus, the reflected light 114r is not allowed to substantially reach the wearer's (user's 103) eyes, and does not cause disturbance. The flexible tongue 39, because of its light absorbing properties, captures reflections of light that cause glare, initiated by the reflective properties within a curved lens/facial shield 102/barrier material. The positioning of the flexible tongue 39 is dynamically maintained between the reflective path from the lamp 37/facial shield 102 and the eyes of the user 103.

In alternative embodiments, shown in FIGS. 28A-28C, a housing 140 includes a lamp 141 comprising a pivotable lens 142, configured to rotate over an angular range about a pivot axis 143. Thus, a light beam 144 can be pivotably oriented from a substantially horizontal position (FIG. 28A) to a superiorly adjusted position (FIG. 28B) and/or to an inferiorly adjusted position (FIG. 28C) without having to pivot the housing 140 and/or having to pivot the entirety of the lamp 141. The upward or downward rotation of the lens 142, aims the light beam 144 accordingly. In an alternative embodiment shown in FIG. 28D, a non-pivotable lens 195 can be used with a pivotable mirror 194 that is pivotable on a pivot axis 193, in order to pivot and aim the light beam 144. In an alternative embodiment shown in FIG. 28E, both the pivotable lens 142 and the pivotable mirror 194 can be used together in order to pivot and aim the light beam 144.

In alternative embodiments, the housing 40 (FIG. 29) at the pivot joint 58 or the lens 142 (FIG. 30) are configured with detents 145, 146 comprising a series of projections 147, 148 that rotate in unison with the housing 40 or the lens 142. In the embodiment of FIG. 29, the clip 84 includes one or more projections 149 and/or depressions 150 that clickingly engage one or more of the projections 147 (e.g., detents), so that as the housing 40 is adjusted, each discrete angular increment is held, until a sufficient force or moment is applied to rotate the housing 40 to a subsequent angular position, in either angular direction. In some embodiments, the detents 145, 146 comprise a two-way ratchet. In some embodiments, the two-way ratchet comprises a spring-loaded ball detent (e.g., utilizing a ball spring).

In the embodiment of FIG. 30, the housing 140 includes one or more projections 151 and/or depressions 152 that clickingly engage one or more of the projections 148, so that as the lens 142 is adjusted, each discrete angular increment is held, until a sufficient force or moment is applied to rotate the lens 142 to a subsequent angular position, in either angular direction.

In other embodiments, as shown in FIG. 31 instead of a contacting mechanical clicking detent, the detents 145, 146 and projections 147, 151, or depressions 152 are replaced by magnetic detents 191, 192, wherein each facing component, housing 40 or clip 84, includes a series of north and south poles. In the embodiment of FIGS. 31A-31C, the series of north and south poles comprise a convex arc and a matching concave arc of north and south poles arrayed along the arcs. Thus, the movement of one component vs. the other component (e.g., via the pivot joint 58) causes alternating attraction and repulsion between the facing poles, thus creating a non-contact clicking or move-stop engagement. In other embodiments, as shown in FIG. 32, a friction between the housing 40 and the clip 84 can be adjustable via a positioning screw 153. Thus, a particular friction force or range of frictional forces can be configured by adjusting the distance along axis X between the housing 40 and the clip 84 with the positioning screw 153. This a concave arc 190 of the clip 84 is moved positively or negatively along axis X to control its amount of normal force applied against a convex arc 189 of the housing 40. Increased normal force produces a proportional increase in the frictional force along the arcs 189, 190. In some embodiments, the frictional force range allows maintenance of the particular angulation of the housing 40 in relation to the clip 84 during use, but is still low enough such that a user is able to adjustingly pivot the housing 40 in relation to the clip 84 about pivot axis 58. In some embodiments, the screw 153 is fully tightenable to a fixed angle, to thus create a very high normal force that does not significantly allow movement of the housing and clip in relation to each other, in order to attain desired performance characteristics.

Figures 33, 34, 35:
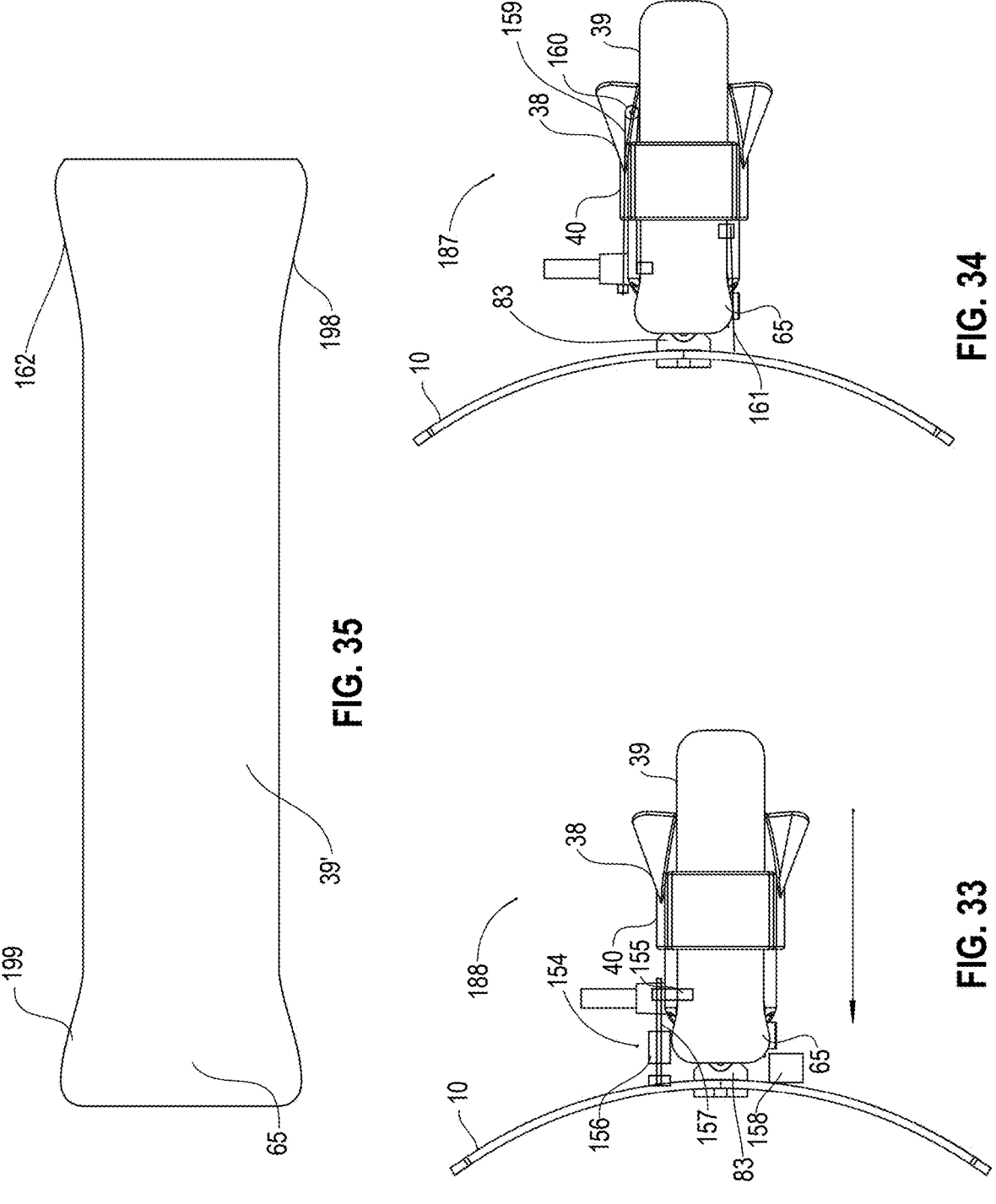
FIG. 33 is a bottom view of the adjustable lamp and glare shield assembly, according to an embodiment of the present disclosure.
FIG. 34 is a bottom view of the adjustable lamp and glare shield assembly, according to an embodiment of the present disclosure.
FIG. 35 is a plan view of a flexible tongue, according to an embodiment of the present disclosure.

In an alternative system 188 as shown in FIG. 33, an actuator 154 is attached to the housing 40 and comprises a movable clamp 155 that statically holds the flexible tongue 39. A motor 156 is attached to the housing 40. A drive train 157 movably couples the clamp 155 with the motor 156, so that output rotation of the motor 156 in a first rotational direction causes the flexible tongue 39 to be moved in a first longitudinal direction, and output rotation of the motor 156 in a second rotational direction, opposite the first rotational direction, causes the flexible tongue 39 to be moved in a second longitudinal direction, opposite the first longitudinal direction (two-headed arrow). The motor 156 can be operated by a microcontroller, and can be voice-activated by verbal commands (e.g., "extend," "retract") via voice recognition technology and/or by controls 158 carried on the system 188. In an alternative system 187 shown in FIG. 34, the flexible tongue 39 is actuated by user-operated pull wires 159, 161, to bi-directionally move the flexible tongue 39. A first pull wire 159 actuates the flexible tongue to extend, via a pulley 160. A second pull wire 161 directly pulls the flexible tongue 39 to retract. In other embodiments, the motor 156 (of the system 188 of FIG. 33) or another motor, can be utilized to automatically raise or lower the orientation of the housing 40 (via the pivot joint 58). The motor can be operated by a microcontroller, and can be voice-activated by verbal commands (e.g., "raise," "lower") via voice recognition technology and/or by controls 158 carried on the system.

Figure 36:
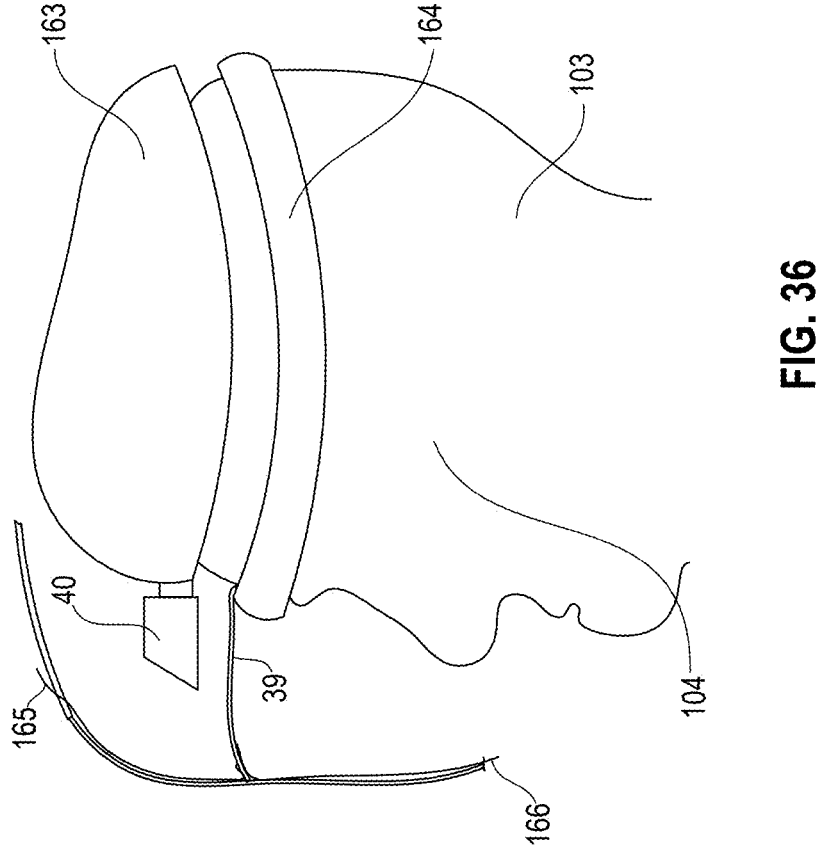
FIG. 36 is a side view of a personal protection system, according to an embodiment of the present disclosure.

An alternative embodiment is illustrated in FIG. 36. The housing 40 is carried on a helmet 163, and a flexible tongue 39 is independently carried on a headband 164. The flexible tongue 39 can be adjustable upwardly via a first traction wire 165 and adjustable downwardly via a second traction wire 166, each of which can be gripped and pulled by the user 103. In some embodiments, the housing 40 can also be adjustable upwardly via the first traction wire 165 and adjustable downwardly via the second traction wire 166.

The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

For purposes of the present disclosure and appended claims, the conjunction "or" is to be construed inclusively (e.g., "an apple or an orange" would be interpreted as "an apple, or an orange, or both"; e.g., "an apple, an orange, or an avocado" would be interpreted as "an apple, or an orange, or an avocado, or any two, or all three"), unless: (i) it is explicitly stated otherwise, e.g., by use of "either . . . or," "only one of," or similar language; or (ii) two or more of the listed alternatives are mutually exclusive within the particular context, in which case "or" would encompass only those combinations involving non-mutually-exclusive alternatives. For purposes of the present disclosure and appended claims, the words "comprising," "including." "having." and variants thereof, wherever they appear, shall be construed as open-ended terminology, with the same meaning as if the phrase "at least" were appended after each instance thereof.

What is claimed is:

1. A system comprising:
   a support configured to be carried by the head of a user;
   a facial shield configured to be coupled to the support such that the facial shield is maintained anterior to the face of the user, the facial shield having substantial clarity for viewing therethrough, the facial shield further comprising an outer surface and an inner surface;
   an emitted-light source configured to be carried between the facial shield and the user and configured to provide a light beam that is able to at least partially radiate through the facial shield; and
   a flexible elongate opaque sheet having a first end coupled to the emitted-light source and a free second end configured to maintain contact with the inner surface of the facial shield as the light beam is angularly adjusted over a working adjustment angle range.

2. The system of claim 1, wherein the opaque sheet is black.

3. The system of claim 1, wherein the emitted-light source comprises a lamp having a housing, and further comprising a pivot configured to allow the housing to rotate about a pivot axis.

4. The system of claim 1, wherein the opaque sheet comprises a polymer.

5. The system of claim 1, wherein the opaque sheet has a thickness of between 0.006 inch and 0.008 inch.

6. The system of claim 3, wherein rotation about the pivot axis in a first rotational direction causes the light beam to be angulated superiorly, and wherein rotation about the pivot axis in a second rotational direction, opposite the first rotational direction, causes the light beam to be angulated inferiorly.

7. The system of claim 6, further comprising:
   one or more contact surfaces carried on the housing and capable of being contacted by the inner surface of the facial shield when the facial shield is coupled to the support and the support is carried by the head of the user, wherein when a first force placed on the outer surface of the facial shield at a first location in relation to the one or more contact surfaces causes the emitted-light source to angulate the light beam superiorly, and wherein when a second force placed on the outer surface of the facial shield at a second location in relation to the one or more contact surfaces causes the emitted-light source to angulate the light beam inferiorly.

8. The system of claim 7, wherein rotation of the housing on the pivot axis includes a rotational resistance of between about 0.2 lbf·in and about 5.0 lbf·in.

9. The system of claim 7, wherein the first force is not less than 0.1 lb.

10. The system of claim 3, wherein the lamp has an illuminance of between 35,000 lux and 105,000 lux.

11. The system of claim 1, wherein the opaque sheet is slidably coupled to the emitted-light source such that the free second end is located at a variable distance from a distal end of the emitted-light source.

12. The system of claim 11, further comprising:

an actuator configured to cause the opaque sheet to be moved in a first longitudinal direction in relation to the emitted-light source.

13. The system of claim 12, wherein the actuator is further configured to cause the opaque sheet to be moved in a second longitudinal direction in relation to the emitted-light source.

14. The system of claim 1, wherein the emitted-light source comprises a lamp and a mount configured to carry the lamp.

15. The system of claim 14, wherein the opaque sheet is slidably coupled to the mount such that the free second end is located a variable distance from a distal end of the mount.

16. The system of claim 15, wherein the mount comprises an arcuate opening having a gap and an arc length, and wherein the opaque sheet comprises a substantially flat working section configured to be slidable within the arcuate opening such that the substantially flat working section is forced into a curve around an opaque sheet longitudinal axis.

17. The system of claim 16, wherein when the working section is slidably moved within the arcuate opening, friction between the working section and the arcuate opening allows the user to adjust the opaque sheet's location in relation to the mount, but maintains the relationship between the opaque sheet and the mount when not being adjusted.

18. The system of claim 15, wherein the opaque sheet is slidable over a length of between 1.5 inches and 2.5 inches.

19. The system of claim 15, wherein the mount comprises an elongate opening having a gap and a width, and wherein the opaque sheet comprises a working section configured to be placed within the elongate opening and slidable therein.

20. The system of claim 19, wherein the opaque sheet comprises a first end width that is greater than the width of the elongate opening, the first end at the first end width configured to act as a stop against the elongate opening to control a maximum extended length of the working section from the elongate opening.

21. The system of claim 19, wherein the working section has a working section width, and wherein the working section width is the same or slightly larger than the width of the elongate opening.

22. The system of claim 1, wherein a distal portion of the opaque sheet, adjacent to the free second end, has an upper surface and a lower surface, the upper surface configured to slide against the inner surface of the facial shield.

23. The system of claim 22, wherein the upper surface comprises a matte finish.

24. The system of claim 1, wherein the opaque sheet comprises a substantially translucent material having an opaque covering.

25. The system of claim 1, wherein the free second end of the opaque sheet comprises a flat transverse distal edge.

26. The system of claim 25, further comprising a first fillet lateral to and at a first side of the flat transverse distal edge, and a second fillet lateral to and at a second side of the flat transverse distal edge.

27. The system of claim 1, wherein a portion of the opaque sheet that is configured to extend from the emitted-light source has a maximum width of 0.9 inch.

28. The system of claim 1, wherein the opaque sheet is configured to be functional for the user's needs via flexure of the opaque sheet, and without any need for trimming of the opaque sheet.

29. The system of claim 1, wherein the system is configured to filter air.

30. The system of claim 3, further comprising:

one or more detents configured to divide rotation about the pivot axis into two or more discrete angular increments.

* * * * *